United States Patent [19]
Reed

[11] Patent Number: 5,744,310
[45] Date of Patent: Apr. 28, 1998

[54] BAX PROMOTER SEQUENCE AND SCREENING ASSAYS FOR INDENTIFYING AGENTS THAT REGULATE BAX GENE EXPRESSION

[75] Inventor: John C. Reed, Rancho Santa Fe, Calif.

[73] Assignee: The Burnham Institute, La Jolla, Calif.

[21] Appl. No.: 688,145

[22] Filed: Jul. 29, 1996

[51] Int. Cl.$^6$ .............................. C12Q 1/68; C12P 21/00; C12N 5/10; C07H 21/04

[52] U.S. Cl. .............................. 435/6; 435/691; 435/91.4; 435/325; 536/24.1

[58] Field of Search .............................. 435/6, 69.1, 91.1, 435/240.2, 91.4, 325; 536/24.1, 23.1

[56] References Cited

U.S. PATENT DOCUMENTS

| | | | |
|---|---|---|---|
| 5,362,623 | 11/1994 | Vogelstein et al. | 435/6 |
| 5,484,710 | 1/1996 | Reed et al. | 435/69.1 |

FOREIGN PATENT DOCUMENTS

| | | |
|---|---|---|
| WO 95/19367 | 7/1995 | WIPO. |

OTHER PUBLICATIONS

Margolis et al. Characterization of cDNA clones containing CCA trinucleotide repeats derived from human brain. Somat. Cell Mol. Genet. 21(4):279–284, Apr. 1995.

Ayer et al., "Mad: A Heterodimeric Partner for Max that Antagonizes Myc Transcriptional Activity," *Cell* 72:211–222 (1993).

Baker et al., "Suppression of Human Colorectal Carcinoma Cell Growth by Wild–Type p53," *Science* 249:912–915 (1990).

Baniahmad et al., "Modular Structure of a Chicken Lysozyme Silencer: Involvement of an Unusual Thyroid Hormone Receptor Binding Site," *Cell* 61:505–514 (1990).

Braxton et al., "Temperature–induced Inversion of Allosteric Phenomena," *J. Biol. Chem.* 269:47–50 (1994).

Christy and Nathans, "Functional Serum Response Elements Upstream of the Growth Factor–Inducible Gene zif268," *Mol. Cell. Biol.* 9:4889–4895.

El–Deiry et al., "Definition of a Consensus Binding Site for p53," *Nature Genetics* 1:45–49 (1993).

El–Deiry et al., "WAF1, a Potential Mediator of p53 Tumor Suppression," *Cell* 75:817–825 (1993).

Fisher et al., "TFEB has DNA–binding and oligomerization properties of a unique helix–loop–helix/leucine–zipper family," *Genes & Devel.* 5:2342–2352 (1991).

Funk et al., "A Transcriptionally Active DNA–Binding Site for Human p53 Protein Complexes," *Mol. Cell. Biol.* 12:2866–2871 (1992).

Ginsberg et al., "Wild–Type p53 can Down–Modulate the Activity of Various Promoters," *Proc. Natl. Acad. Sci, USA* 88:9979–9983 (1991).

Gregor et al., "The adenovirus major late transcription factor USF is a member of the helix–loop–helix group of regulatory proteins and binds to DNA as a dimer," *Genes & Devel.* 4:1730–1740 (1990).

Harper et al., "The p21 Cdk–Interacting Protein Cipl is a Potent Inhibitor of G1 Cyclin–Dependent Kinases," *Cell* 75:805–816 (1993).

Hartwell, "Defects in a Cell Cycle Checkpoint May Be Responsible for the Genomic Instability of Cancer Cells," *Cell* 71:543–546 (1992).

Howe et al., "Characterization of the sequence–specific interaction of mouse c–myb protein with DNA," *Embo J.* 9:161–169. (1990).

Kasten et al., "A Mammalian Cell Cycle Checkpoint Pathway utilizing p53 and GADD45 is Defective in Ataxia–Telangiectasia," *Cell* 71:587–597 (1992).

Kitada et al., "γ–Radiation induces upregulation of Bax protein and apoptosis in radiosensitive cells in vivo," *Oncogene* 12:187–192 (1996).

Knudson et al., "Bax–Deficient Mice with Lymphoid Hyperplasia and Male Germ Cell Death," *Science* 270:96–99 (1995).

Krajewski et al., "Upregulation of Bax Protein Levels in Neurons following Cerebral Ischemia," *J. Neuroscience* 15:6364–6376 (1995).

Kuriyan and Thanos, "Structure of the NF–kB transcription factor: a holistic interaction with DNA," *Structure* 3:135–141 (1995).

Lotem and Sachs, "Regulation of bcl–2, bcl–$X_L$ and bax in the Control of Apoptosis by Hematopoietic Cytokines and Dexamethasone," *Cell Growth Diff.* 6:647–653 (1995).

Lowe, "Cancer therapy and p53," *Curr. Opin. Oncol.* 7:547–553 (1995).

Mietz et al., "The Transcriptional Transactivation Function of Wild–Type p53 is Inhibited by SV40 Laarge T–Antigen and by HPV–16 E6 Oncoprotein." *Embo J.* 11:5013–5020 (1992).

Miyashita et al., "Identification of a p53–Dependent Negative Response Element in the bcl–2 Gene," *Cancer Res.* 54:3131–3135 (1995).

Miyashita et al., "Tumor suppressor p53 is a regulator of bcl–2 and bax gene expression in vitro and in vivo," *Oncogene* 9:1799–1805 (1994).

Miyashita and Reed, "Tumor suppressor p53 is a Direct Transcriptional Activator of the Human bax Gene," *Cell* 80:293–299 (1995).

(List continued on next page.)

*Primary Examiner*—Nancy Degen
*Assistant Examiner*—William Sandals
*Attorney, Agent, or Firm*—Campbell & Flores LLP

[57] ABSTRACT

The present invention provides a substantially purified bax promoter and a nucleic acid molecule containing a nucleotide sequence encoding a gene product operably linked to a bax promoter. The invention also provides a substantially purified active fragment of a bax promoter and a nucleic acid molecule containing a nucleotide sequence encoding a gene product operably linked to an active fragment of a bax promoter. Cell-based screening assays for identifying an effective agent such as a drug that regulates the level of expression of a gene operably linked to a bax promoter, or an active fragment thereof, also are provided.

25 Claims, 7 Drawing Sheets

OTHER PUBLICATIONS

Oltvai et al., "Bcl-2 Heterodimerizes In Vivo with a Conserved Homolog, Bax, that Accelerates Programed Cell Death," *Cell* 74:609–619 (1993).

Pognonec et al., "The Helix–Loop–Helix/Leucine Repeat Transcription Factor USF can be Functionally Regulated in a Redox–dependent Manner," *J. Biol. Chem.* 267:24563–24567 (1992).

Prives and Manfredi, "The p53 Tumor Supressor Protein: Meeting Review," *Genes and Devel.* 7:529–534 (1993).

Sen and Baltimore, "Multiple Nuclear Factors Interact with the Immunoglobulin Enhancer Sequences," *Cell* 46:705–716 (1986).

Stenger et al.,"p53 oligomerization and DNA looping are linked with transcriptional activation," *Embo J.* 13:6011–6020 (1994).

Unger et al., "p53: a Transdominant Regulator of Transcription Whose Function is Ablated by Mutations Occurring in Human Cancer," *Embo J.* 11:1383–1390 (1992).

Wang et al., "Wild–type p53–Triggered Apoptosis is Inhibited by bcl-2 in a v–myc–Inducet T–cell Lymphoma Line," *Oncogene* 8:3427–3431 (1993).

White, "Life, death, and the pursuit of apoptosis," *Genes & Devel.* 10:1–15 (1996).

Yonish–Rouach et al., "Wild–type p53 induces apoptosis of myeloid leukaemic cells that is inhibited by interleukin–6," *Nature* 352:345–347 (1991).

Young and Korsmeyer, "A Negative Regulatory Element in the bcl–2 5"–Untranslated Region Inhibits Expression from an Upstream Promoter," *Mol. & Cell. Biol.* 13:3686–3697 (1993).

Yu et al., "Gene expression in astrocytes during and after ischemia," *Prog. Brain Res.* 105:245–253 (1995).

Zervos et al. "Mxil, a Protein That Specifically Interacts with Max to Bind Myc–Max Recognition Sites," *Cell* 72:223–232 (1993).

Zhan et al., "Induction of Cellular p53 Activity by DNA–Damaging Agents and Growth Arrest," *Mol. Cell. Biol.* 13:4242–4250 (1993).

-3885                GGATC CCTTGAGCCC AGGAGGTCGA GGTGGCAGTG

AGCCACAGTT GTGTCATTGC ACTCCAGCCT GGACGACAGA GGGAGATCCT     -3801
        c-Myb

GTCTCAAAAT AAATAAATAA AAATAAAAAT AAACAGTTTT GACTTCACAA

CTAGCTAAAA AGTGTATTCC CTCACTCAGT GACTGTACTG TTCAGAGGTG     -3701

TATACCTGCA TTAAAAGCCC TTTCCTTCCT TCTCTGTAAC TGGAGTAGGG
                                         v-Myb

Oct-1
   AAGGGCTATC TCATTGGACT GGAGTAACAC ACACAGATAA AGCCGGATGC     -3601
                                                   Ets-1

AAAGTTAACA GGAAACACTA TTTCTCTCAA GGATACGCTT TGTTTGTTTT
       PEA3

TTTTTTGAGA TGAAGTCTCG CTCTGTCACC CGAGGTGGAG TGCAATGGCA     -3501

CGATCTCTGC TCACTGCAGN CTCTGCCTCC TGGGTTCAAG TGATTCTCTG

GCCTCAGCCT CCCAAGTAGC TGGGATTACA GGAGCGCACC AGTACGCCCA     -3401

GCTAATTTTT GNATTTTTAG TAGAGACAGG GTTTCACCAT GTTGGCCAGG

FIG. 1A

```
CTGGTCTCAA ACTCCTGACC TCAGGTGATC TNCCTGTCTT GGNCTCCCAA      -3301

AGTGGTGGGA TTTCAGGTGT GAGCCACCAC GCTGGCCAAG GACATGGTTT

CTTACAGAGA CTTTGTTCTC TAAATTCATA AATTGTTGGA AATTCTATCA      -3201

GTAAAAATGA AACATCCGAG TCTTGCTGAC AGGATCTAAT CCACTTGATA

CAGAGTAGCA GCCTTGATTT CCAAAGCAGG TGCACAGCTT CAGATAAAGG      -3101

GTTTCTGGAT GCAACATTTC ACATGTACCT TCTTGTTTCC AGCGATTCAG

GACACTGGTT TCACTTCACA GTCCTGATCC AATGTTGACC TTGCTTTGCT      -3001

CTAAGCTATC ATTTGGTTGT CACCTAAGCT CTACCCTCCC CCTTTATCTT

GGCTTTTTCT TTTCTTTTTT CTTTTTGAGA CAGGCTCTTC CTCTGTCACC      -2901

CAGTCTGATT GCAGTGATGC AATTGATCAC AGCTCACGGC AGCCGGGACC
                     ‾‾‾‾‾‾‾‾‾‾‾‾‾‾‾‾‾‾‾‾
                          NF-IL-6

TCCCAAGCTC AAACAATCTT CCCACCTCAG CCTCCCAAGT AGCTGGGACT      -2801

ACAGGCACGC ACCACCACAT CCAGCTAATT TTCTTTTTTT TCTGCTTCCT
```

FIG. 1B

```
TTTCTTTTTG TTTTTTTTTN AGATAGAGGC TTGCTCTGTT GCCCAGGCTG        -2701
                                 ━━━━━━━━━━ ━━━━━━━━━━
                                    p53         p53

GGGTGCAGTG GCACGATCTT GGCTCACTGC AACCTCTGCC TCTTGGGTTC
━━━━━━━━━━

AAGCGATTCT CCTGCCTCAG CCTCCCAAGC AGCTGGGACT GCAGGCACGC        -2601

GCCACCACTC CCAGCTAATT TTTTTGTATT TTTAGTGGAG ACGGGGTTTC

GCCATGTTGG CTAGGCTGGT CACAAACTCC TGACCTCAGA TGATACACCC        -2501
                     ━━━━━━━━━
                        ERE
                      half-site

ACTTCGGCCT CCCACACAGC TGGTATTACA GGTGTGAGCT ACCACGCCCG

GCCCCCCCTC CTTTCTTTTG TTTTTTAGTT GACACAGGGT CTCACCATGG        -2401

TACAGCCCAG GCTGGTCCTG AACTCCTGGC TTCAGGTGAT CCTCCTGCCT

MyoD
                                            ━━━━━━
TGGCCTCCCA AAGTGCTGGG ACTATAGGAA TGAGCCATCA CACCTGGCCC        -2301

CTTTCTTCAA TTTTCAAATC AAACTGATCC TTCAAGGTCA AGAGGAAATA
                                    ━━━━━━━━ ━━━━━━━━
                                      ERE      PEA3
                                    half-site

CCTCCTCTGA GAAGTCTTCT CTGAATGTCA GAGGCAGACA ATGTTTGATT        -2201
```

FIG. 1C

```
TCTGCATGCT CCCCAACATT CAATCATACA GTTATTGAAT AACACATTTT
                             ─────────── ──────────
                                c-Myb       AP-1

GAGAGATAAC TATGAATCAA GTAACATGCT GGTTTCTGGG AGNAATTGAG                -2101
           ──────────
             AP-1

GACAAATTAA CCTTGTGGAA ATTTTGGGTG GATGAAAAAA ACCAACATTA
           ──────────
            NF-IL-6

AATTAAAACA CTGCACACAT TTACAGCTGT GAGAAGCATT ACACATCCTG                -2001

GGTGCTATGC GAGCTTTTTT TTTTTTTTTT TTTTTTTGGA GTTGGAGTTT

CCCTCTTGTT ACTGAGGCTG GAGAGCAAGG TCACGATCTC GGCTCACTGC                -1901
                                 ──────────
                                    ERE
                                 half-site

AACCTCTGCC TCCAGATTCA AACGATTCCC CTGCCTCAGC TCCCGAGTAG

CTGGGACTAC AGGTGCCTGC CACCACACCT GGCTAATTTA GAATTTTTAG                -1801
                      ──────────
                         MyoD

TAGGGATAGG GTTTCACCGT GTTGGCCAGG CTGGTCTCAA ACTCCTGACC

TCAGGTGATC TACCCATCTC GGNCTCCCAA AGTGCTGGGA TTACAGAAGT                -1701

GAGCCACTGA GCCCAACCAG GAGCTTTTTC GAGAAAGAAG GAAGTCCAAG
                                            ──────────
                                               PEA3
```

FIG. 1D

```
AGATCTTCCT GACACCCTAG TCTGACTCTG CCCTTTGSCT GCTCAAAATT      -1601

TCCCCATGCT TCCCAGCGGS CTTCTGGACA TAGATCAAGT CCCTTCTCTG

ACAGGCCCAA ACCCTTTATC ATCTGATCCT AGCTCATTTT TCTGAGTTTT      -1501

CCTTAGTTGC TATTATTTTC TGTCTAAAGT GACATGTCAT AATATTCATA
                                                 ‾‾‾‾‾‾‾‾‾‾
                                                   Pit-1

AAGCACACAA GTCTTATGTG TACAGCTCAA TGAATTGTAA ATATGTGTAT      -1401

WCCCGGCCGG GCACAGTGGC TCACGCCTGT AATCCCAGCA CTTTGGGAGG

GCGAGGCAGG TGGATCACTT GAGGTCAGGA GCTTGAGACC AGCCTGACCA      -1301
                      ‾‾‾‾‾‾‾‾‾‾
                         ERE
                       half-site

ACATAGTGAA ACCCCATCTT TACTAAAAAT ACAAAATTAG CTGGGCGTGG

TGTCGCATGC CTGCAATTCC AGCTACTTGG GAGGCTGAGG CAGGAGAATT      -1201

GCTTGAACCC GGAGGCAGAG GTTGCAGTAA GCCAAGATCG TGCCATTGCA
                                ‾‾‾‾‾‾‾‾‾‾
                                 NF-IL-6

CTCCATCCTG GGCAACAAGA GCAAAACTCC GTCTCAAAAT AATAATAATA      -1101
```

FIG. 1E

```
ATAATAATAA TAATAATAAT AATAATAATA ATAATAATGT GTATACCCAT

GTAAACACCA TTCAGATAAA AATATGGCAT ATTTGGGGCA CCCGGGGAGT         -1001

GTCTCTTGTG GCCCCTCCCC TCCATACCCT GCTGATCTAT CAGCACAGAT

TAGTTTCTGC CACTTTTTAA ACTTCATATT CCTTTTCTTT TTACACAAAC         -901

ACAAACATTC GAGTCATGAC TGGGTGGGGT GGCTCAAGCC TGTAATCTCA

GCACTTTGGG AGGCCAAGGT GCGAGGATCG CTTGAGTCTG GGAGTTCAGA         -801

GACCAGCCTG GGCAACATAG AGAGACCTCA TCTCCACATA AAAAGTTTTA

AAAATTAACC AGGGGCGGTG TAGTCCCAGC TACTCAGGAG GCTGAGGTGG         -701

GAGGCTTCAG CCCGGGAATT CCAGACTGCA GTGAGCCATG ATTGGGCCAC
   NF-κB         NF-κB                                 NF-κB

TGCACTCCAG CCTGGGCAAC ACAGTGAGAC CCTGTCTCAA AAAAAAAAA          -601

AAAAAAAAAA AAAAAAACAG GAAAAAACAA ACAAACAGAA AAGCAGGCCT
                PEA3
```

FIG. 1F

```
GGCGCGGTAG CTCATGCCTG TAATCCCAGC GCTTTGGAAG GCTGAGACGG        -501 p53
GGTTATCTCT TGGGCTCACA AGTTAGAGAC AAGCCTGGGC GTGGGCTATA
                 p53        p53         p53

TTGCTAGATC CAGGTCTCTG CAAAAAACAA AACCACTCAG TTTTTAGTCA        -401

⇓
TCTATAACGT CCTGCCTGGA AGCATGCTAT TTTGGGCCTC TGAGCTTTTG
   TATA

CACTTGCTAA TTCCTTCTGC GCTGGGAGA GCTCAAACCC TGCCCGAAAC         -301

TTCTAAAAAT GGTGCCTGGA TAAATGAAGG CATTAGAGCT GCGATTGGAC

GGGCGGCTGT TGGACGGCGC CACTGCTGGC ACTTATCGGG AGATGCTCAT        -201

TGGACAGTCA CGTGACGGGA CCAAACCTCC CGAGGGAGCG AGGCAGGTGC

GGTCACGTGA CCCGGCGGCG CTGCGGGGCA GCGGCCATTT TGCGGGGCGG        -101
ERE
half-site
 CCACGTGAAG GACGCACGTT CAGCGGGGCT CTCACGTGAC CCGGGCGCGC
                              NF-κB TGCGGCCGCC CGCGCGGACC CGGCGAGAGG CGGCGGCGGG AGCGGCGGTG         -1
    Egr-1
```

FIG. 1G

BAX PROMOTER SEQUENCE AND SCREENING ASSAYS FOR INDENTIFYING AGENTS THAT REGULATE BAX GENE EXPRESSION

This work was supported by grant CA60181 awarded by the National Cancer Institute. The United States Government has certain rights in this invention.

BACKGROUND OF THE INVENTION

FIELD OF THE INVENTION

This invention relates generally to the fields of apoptosis and gene regulation and more specifically to the regulatory sequence of a bax gene involved in cell death.

BACKGROUND INFORMATION

Cell death occurs by a variety of processes including, for example, programmed cell death and necrosis. The term "apoptosis" describes the morphological features of a cell undergoing the process of programmed cell death, which is responsible for maintaining a steady-state level of cells in a self-renewing tissue. Under normal conditions, apoptosis assures that the number of dying cells in a tissue is roughly equivalent to the number of newly produced cells. However, in various disease states or as a result of an insult to a tissue, dysregulation of the process of apoptosis can occur. In addition, various disease states are associated with an abnormal level of cell death due to processes other than apoptosis.

In Alzheimer's disease, Parkinson's disease, Huntington's chorea, epilepsy, amyotrophic lateral sclerosis, stroke, ischemic heart disease, spinal cord injury or one of many viral infections, for example, an abnormally high level of cell death occurs. In at least some of these conditions, there is evidence that the excessive cell death occurs through a mechanism consistent with apoptosis. Among these are 1) spinal cord injury, where the severing of axons deprives neurons of neurotrophic factors necessary to sustain cellular viability; 2) stroke, where after an initial phase of necrotic cell death due to ischemia, the rupture of dead cells releases excitatory neurotransmitters such as glutamate and oxygen free radicals that stimulate apoptosis in neighboring healthy neurons; and 3) Human Immunodeficiency Virus (HIV) infection, which induces apoptosis of T-lymphocytes.

In contrast, the level of apoptosis can be reduced in a cancer cell, which allows the cancer cell to survive longer than its normal cellular counterpart. As a result of the increased number of surviving cancer cells, the mass of a tumor can increase even if the doubling time of the cancer cells does not increase. Furthermore, a cancer cell that expresses a high level of the bcl-2 gene, which is involved in regulating cell death, is rendered relatively resistant to chemotherapeutic agents and to radiation therapy.

The molecular mechanisms that regulate cell death are not well understood. It now is becoming clear, however, that several proteins such as Bcl-2 and a Bcl-2-related protein, termed "Bax," have a central role in apoptosis. Specifically, the expression of Bcl-2 in a cell blocks apoptosis, whereas the expression of Bax in a cell promotes apoptosis. For example, when Bcl-2 levels in a cell are decreased or when Bax levels are elevated, the rate of cell death is accelerated. Conversely, when Bcl-2 levels in a cell are increased or when Bax levels are decreased, apoptosis is inhibited. Thus, it is the relative levels of proteins that are involved in apoptosis, such as Bcl-2 and Bax, that determine whether a cell survives or is fated to undergo programmed cell death.

The p53 tumor suppressor protein (p53) is another example of a protein that is involved in the process of apoptosis. Wild-type p53 protein induces apoptosis in a cell, whereas many mutant p53 proteins have lost the ability to induce apoptosis. Many cancers have mutations in the genes encoding p53 and, therefore, either do not express any p53 protein or express a mutant form of p53. Thus, the absence of wild-type p53 tumor suppressor in a cancer cell can contribute to a low level of apoptosis, allowing the cancer cell to have a longer life span than its normal cellular counterpart.

The ability to manipulate the rate of programmed cell death due, for example, to regulation of bax gene expression, can provide physicians with a means of ameliorating the effects of a disease that is characterized by an abnormal level of cell death. For example, the isolation of a nucleic acid sequence that regulates bax gene expression would allow the development of a method of identifying an agent that effectively regulates bax gene expression and, thus, the level of apoptosis in a cell. However, only a small fragment of the nucleic acid sequence that controls bax gene expression currently is available. Thus, there exists a need to isolate the entire nucleic acid sequence that controls bax gene expression and to develop a method of identifying an agent that effectively regulates bax gene expression and, consequently, apoptosis. The present invention satisfies this need and provides related advantages as well.

SUMMARY OF THE INVENTION

The present invention provides a substantially purified bax gene promoter having the nucleotide sequence shown as position -3885 to position -1 in FIG. 1 (SEQ ID NO: 1) or the nucleotide sequence shown as position -3885 to position -974 in FIG. 1 (SEQ ID NO: 1). The invention also provides a nucleic acid molecule containing a nucleotide sequence encoding a gene product operably linked to a bax promoter.

The present invention further provides methods of using a gene such as a reporter gene operably linked to a bax promoter in a cell-based screening assay for identifying an effective agent that regulates the level of expression of a gene operably linked to the bax promoter or an active fragment thereof. Such an effective agent can be identified according to a method of the invention by introducing into the cell a nucleic acid molecule containing the gene operably linked to the bax promoter or the active fragment thereof; determining a control level of expression of the gene in a cell containing the gene; contacting a cell containing the gene with an agent suspected of being an effective agent; and determining a test level of expression of the gene in the cell contacted with the agent, where a difference in the test level of expression as compared to the control level of expression identifies the agent as an effective agent. An effective agent that is identified according to a method of the invention can be, for example, a drug that reduces or inhibits bax gene expression in a neuron and, therefore, is useful in treating a neuronal disease characterized by an abnormally high level of apoptosis. An effective agent also can be, for example, a drug that increases bax gene expression in a tumor cell and, therefore, is useful in treating a tumor characterized by an abnormally low level of apoptosis.

BRIEF DESCRIPTION OF THE DRAWINGS

FIG. 1 shows the nucleotide sequence of the entire human bax promoter (SEQ ID NO: 1). The "A," "C," "G" or "T" single letter code represents adenine, cytosine, guanine or thymine, respectively, while "S" represents guanine or cytosine and "W" represents adenine or thymine. The approximate transcription start site is indicated by an arrow. p53 binding sites, consisting of two or more 10 bp sequences, which can be perfect or imperfect matches to the p53 consensus sequence, are shown in FIG. 1. Perfect (10/10 matches) consensus p53 sequences are indicated by double overlining and double underlining, while imperfect p53 sequences are indicated by single underlining or overlining. Hexameric CACGTG repeats are indicated by double overlining. The TATAA box and binding sites for c-Myb, v-Myb, Ets-1, Oct-1, PEA3, NF-IL-6, estrogen receptor, MyoD, AP-1, Pit-1, NF-κB and Egr-1 are indicated by single underlining or overlining.

DETAILED DESCRIPTION OF THE INVENTION

The present invention provides a substantially purified bax promoter having the nucleotide sequence shown as position -3885 to position -1 in FIG. 1 (SEQ ID NO: 1) or the nucleotide sequence shown as position -3885 to position -974 in FIG. 1 (SEQ ID NO: 1).

The bax gene encodes a protein that is a member of the Bcl-2 family of proteins as indicated by homology between the Bax and Bcl-2 amino acid sequences (Reed, *Curr. Opin. Oncol.* 7:547-553 (1995); White, *Genes Dev.* 10:1-15 (1996)). Bax associates with Bcl-2 in cell extracts in vitro and suppresses the ability of Bcl-2 to block apoptosis (Oltvai et al., *Cell* 74:609-619 (1993)). In Bax-deficient mice, thymocytes and B cells display hyperplasia, further supporting a role for Bax in cell death (Knudson et al., *Science* 270:96-99 (1995)). Since Bax functions to promote apoptosis, regulation of bax gene expression provides a means to modulate the level of apoptosis in a cell.

Although Bax promotes cell death in most cellular contexts, gene targeting experiments in mice indicate that in some cell types Bax can promote cell survival. For example, in the testes, Bax can be required for the survival of cells necessary for normal spermatogenesis (Knudson et al., supra, 1995). Thus, in some circumstances, it can be desirable to increase Bax expression to protect particular tissues from cell death.

The present invention provides a substantially purified bax promoter. The nucleotide sequence of the entire human bax promoter, which can regulate bax gene expression and, thus, apoptosis of a cell, is shown in FIG. 1 (SEQ ID NO: 1). As used herein, the term "bax promoter" means the nucleotide sequence shown as positions -3885 to -1, including the nucleotide sequence shown as positions -3885 to -974 in FIG. 1 (SEQ ID NO: 1), which confers regulatory activity upon an operably linked gene as described below. The term "entire bax promoter" as used herein refers to the nucleotide sequence shown as positions -3885 to -1 in FIG. 1 (SEQ ID NO: 1). The entire bax promoter (SEQ ID NO: 1) contains about 3885 nucleotides, including a TATAA box at positions -398 to -394, a transcription start site about 22 bp downstream of the TATAA box and about 370 nucleotides of 5'-untranslated region (5-UTR).

As used herein, the term "substantially purified," when used in reference to a bax promoter, means that the bax promoter is in a form that is relatively free from contaminating lipids, proteins, unrelated nucleic acids or other cellular material normally associated with a bax promoter. A substantially purified bax promoter, for example, is in a form that is relatively free from chromatin.

The bax promoter disclosed herein contains nucleotide sequences that act as regulatory elements (also known as "responsive elements") to control bax gene expression. A regulatory element is characterized, in part, in that it regulates expression of a linked gene and is activated due to the binding or release of a transcription factor. Numerous examples of regulatory elements and transactivating factors are disclosed herein or otherwise known in the art.

The bax promoter disclosed herein contains, for example, a p53 responsive element (p53-RE), which is bound by the p53 tumor suppressor protein to up-regulate gene expression (see, for example, U.S. Pat. No. 5,484,710, issued Jan. 16, 1996, which is incorporated herein by reference; see, also, below). The sequence shown as positions -485 to -449 of the bax promoter (SEQ ID NO: 2), for example, confers the regulatory activity of a p53-RE as defined herein. The distal region of the ax promoter shown as positions -2724 to -2697 in FIG. 1 (SEQ ID NO: 1) also contains a p53-RE that can confer responsiveness to the p53 tumor suppressor. As used herein, the term proximal refers to a region that is relatively close to the transcription start site of a promoter, while the term distal refers to a region that is relatively farther from the transcription start site.

The p53 tumor suppressor is a 53 kilodalton (kDa) nuclear phosphoprotein that can induce transcription of various genes by binding to a consensus DNA binding site within the gene or can inhibit transcription by interacting, for example, with other transcription factors required for expression of a gene (Zhan et al., *Mol. Cell. Biol.* 13:4242–4250 (1993), which is incorporated herein by reference). The p53 protein contributes to tumor suppression through at least two mechanisms, arrest of cellular proliferation and induction of apoptosis (see Hartwell, *Cell* 71:543–546 (1992); Yonish-Rouach et al., *Nature* 352:345–347 (1991); Baker et al., *Science* 249:912–915 (1990)). Recently, potential pathways to explain the mechanism by which p53 arrests cellular proliferation have been suggested (Harper et al., *Cell* 75:805–816 (1993); El-Deiry et al., *Cell* 75:817–825 (1993)). However, the mechanism by which p53 induces apoptosis has not yet been described.

The term "p53-responsive element" is synonymous with "p53-RE" and refers to a cis-acting, position-independent DNA sequence that is required for regulation of a gene by the p53 tumor suppressor. A p53-RE is considered to be a cis-acting regulatory element because it must be linked to a gene in order to confer p53-mediated regulation upon the gene. In addition, a p53-RE is considered to be a position-independent element because it is active regardless of whether it is located upstream or downstream of the promoter of the gene which it regulates.

Regulation of a gene such as a bax gene that contains a p53-RE is mediated, in part, by the p53 tumor suppressor. As used herein, the term "p53-mediated regulation" means regulation mediated by the wild-type p53 tumor suppressor protein through a p53-RE. As shown in Example I, expression of wild-type p53 tumor suppressor in a cell results, for example, in an increase in bax mRNA and protein in a cell, which, in turn, promotes cell death.

53-mediated regulation can be due to direct binding of the p53 tumor suppressor to a p53-RE or can be due to p53 interacting with one or more additional proteins, any or all of which can bind to a p53-RE to cause regulation of the gene. A p53 binding site has been described in several genes that are induced by p53 (El-Deiry et al., supra, 1993; El-Deiry et al., *Nat. Genet.* 1:45–49 (1992), each of which is incorporated herein by reference).

A p53 binding site contains two or more of the 10 base pair (bp) consensus p53 sequences:

5'-Pu-Pu-Pu-C-(A/T)-(T/A)-G-Py-Py-Py-3'(SEQ ID NO: 3;

where "Pu" indicates a purine and "Py" indicates a pyrimidine) separated by 0 to 13 bp (El-Deiry et al., supra, 1992). For convenience, the term "consensus p53 sequence" is used to refer to one 10 bp sequence shown as SEQ ID NO: 3. However, it should be recognized that, for p53 binding to occur, a p53 binding site must contain at least two of the 10 bp consensus p53 sequences shown as SEQ ID NO: 3. As used herein, reference to "a perfect match" of the consensus p53 sequence means a 10 bp sequence that contains a nucleotide sequence encompassed within the consensus sequence shown as SEQ ID NO: 3, whereas reference to an "imperfect" consensus p53 sequence means a 10 bp sequence wherein at least one nucleotide is different from the consensus sequence shown as SEQ ID NO: 3.

The p53-RE (SEQ ID NO: 2) shown as positions -485 to -449 of the bax promoter in FIG. 1, which contains one 10 bp sequence that is a perfect match to the consensus p53 sequence and three imperfect consensus p53 sequences, can bind p53 (see Example II). A p53-RE also can consist of one perfect match of the consensus p53 sequence and at least one imperfect p53 sequence. As disclosed herein, the distal region of the bax promoter shown as positions -2724 to -2697 in FIG. 1 (SEQ ID NO: 1) also can be a p53-responsive element.

A p53-RE regulates expression of a linked gene. For example, a p53-RE$^U$ element is a positive regulatory element, which, when activated by p53, up-regulates the level of transcription of a linked gene. The p53-RE disclosed, for example, in the -485 to -449 region of the bax promoter (SEQ ID NO: 2) is a p53-RE$^U$. In contrast, a p53-RE$^D$ down-regulates the level of transcription of a linked gene (see, for example, U.S. Pat. No. 5,484,710, supra).

In addition to a p53-responsive element, other regulatory elements also can be involved in controlling bax gene expression. For example, expression of wild-type p53 is sufficient to induce apoptosis in some p53-deficient tumor cell lines, as indicated by spontaneous cell death following p53 expression (see, for example, Yonish-Rouach et al., supra, 1991; Shaw et al., Proc. Natl. Acad. Sci., USA 89:4496–4499 (1992)). However, restoration of p53 activity, alone, is not sufficient to trigger apoptosis in other p53-deficient tumor cell lines although it can render such cell lines relatively more sensitive to induction of apoptosis by radiation and DNA-damaging chemotherapeutic drugs (see, for example, Fisher, Cell 78:539–542 (1994)). These results indicate the cell-type specific nature of p53-mediated gene regulation and show that factors other than p53, alone, can be involved in regulating expression of a gene involved in apoptosis such as a bax gene.

Studies relating to the differential sensitivity of various cell types to γ-radiation confirm that the p53 tumor suppressor, alone, may not be sufficient to upregulate bax gene expression in all cell types. In several cell types such as lymphoid and small intestinal cells, radiation induces a p53-mediated increase in the level of bax gene expression. In other cell types, however, bax gene expression is not increased following irradiation, although a p53-dependent elevation occurs in another p53 target gene, waf-1 (Kitada et al., Oncogene 12:187–192 (1996)). Thus, in some cell types, the induction of p53, as indicated by elevated waf-1 expression, is not sufficient to upregulate bax expression. These results demonstrate the relevance of additional regulatory factors, especially cell-type specific factors, to the regulation of bax expression.

Analysis of tissues from p53 "knock-out" mice also indicates that regulatory factors in addition to the p53 tumor suppressor can be important in determining bax gene expression. In mice lacking the p53 tumor suppressor, Bax protein levels are markedly reduced in prostate epithelium, central and peripheral neurons and small intestine, but not in other tissues examined (Miyashita et al., Oncogene 9:1799–1805 (1994a), which is incorporated herein by reference). Thus, in the absence of p53, tissue-specific factors can be involved in influencing bax gene expression in vivo.

In addition to the p53-responsive elements discussed above, the bax promoter disclosed herein contains other regulatory elements that can be important in modulating bax gene expression. For example, the bax promoter contains four C-A-C-G-T-G motifs located within the 5'-UTR. Each of these hexameric elements represents a potential binding site for several different transcription factors, including, for example, Myc and its homologs (see, for example, Zervos et al., Cell 72:223–232 (1993); Ayer et al., Cell 72:211–222 (1993)) and USF, which is a ubiquitously-expressed transcription factor whose activity is controlled by redox mechanisms (Pognonec et al., J. Biol. Chem. 267:24563–24567 (1992)).

Myc can induce apoptosis in response to serum-deprivation in fibroblasts or following antigen-receptor cross-linking in T cell hybridomas (see, for example, Asken et al., Oncogene 6:1915–1922 (1992)). The presence of Myc binding sites in the bax promoter (SEQ ID NO: 1) indicates that Myc can up-regulate bax gene expression, thereby leading to apoptosis.

Additional regulatory elements also are located within the bax promoter disclosed herein (see FIG. 1). For example, c-Myb binds the sequence C-A/C-G-T-T-Pu (see Howe et al., EMBO J. 9:161–9 (1990), which is incorporated herein by reference); the bax promoter contains such c-Myb binding sites at positions -3845 to -3840 (C-A-G-T-T-G) and -2172 to -2167 (C-A-G-T-T-A) as shown in FIG. 1 (SEQ ID NO: 1). A v-Myb binding site also is located on the complementary strand at positions -3664 to -3659 of the bax promoter (SEQ ID NO: 1) as shown in FIG. 1. Since expression of c-Myb accelerates TGF-β1 induced apoptosis in myeloid leukemia cells (Selvakumaran et al., Mol. Cell. Biol. 14(4):2352–2360 (1994)), Myb can play a role in inducing apoptosis. The presence of c-Myb regulatory elements in the bax promoter indicates that Myb can regulate apoptosis by up-regulating bax gene expression.

The bax promoter (SEQ ID NO: 1) further contains the sequence T-G-A-A-T-A-A at positions -2165 to -2159 and the sequence T-G-A-A-T-C-A at positions -2138 to -2132, each of which can be a responsive element for the transcription factor complex AP-1, which binds the consensus sequence T-G-A-N-T-A/C-A, where "N" indicates any nucleotide (Yu et al., Prog. Brain Res. 105:245–53 (1995), which is incorporated herein by reference). The protein c-Jun, which is one component of the AP-1 complex, can promote apoptosis in some cellular contexts such as in adult neurons or myeloid leukemia cells (see, for example, Dragunow and Preston, Brain Res. Rev. 21:1–28 (1995)). The presence of AP-1 regulatory elements in the bax promoter indicates that c-Jun can be involved in promoting apoptosis by up-regulating bax gene expression.

The bax promoter disclosed herein further contains nucleic acid sequences related to the regulatory element for NF-κB, which originally was discovered as a lymphoid specific protein that bound the sequence G-G-G-A-C-T-T-C-C (Sen and Baltimore, Cell 46:705–716 (1986)). The NF-κB regulatory element consensus sequence is G-G-G-

Pu-N-N-Py-Py-C-C (Kuriyan and Thanos, *Structure* 3:135–141 (1995)). Potential NF-κB binding sites within the bax promoter (SEQ ID NO: 1; FIG. 1) include the sequences G-G-G-A-A-T-T-C-C (positions -687 to -679); G-G-G-G-C-T-C-T-C (positions -76 to -68); G-G-G-A-G-G-C-T-T-C (positions -702 to -693); and G-G-G-C-C-A-C-T-G-C (positions -657 to -648). The transcription factor NF-κB can be involved in apoptosis since, for example, activation of NF-κB is correlated with apoptosis induced by tumor necrosis factor-αor cancer chemotherapeutic agents such as 1-β-D-arabinofuranosylcytosine in leukemia cell lines (see, for example, Beg et al., *Mol. Cell. Biol.* 13:3301 (1993); Kuwakado et al., *Leuk. Res.* 19(9) :645–650 (1995)). Furthermore, an inhibitor of NF-κB activation prevents apoptosis (Bessho et al., *Biochem. Pharmac.* 48:1883 (1994) ). The presence of binding sites for NF-κB in the bax promoter therefore indicates that NF-κB can promote apoptosis by up-regulating bax gene expression.

The transcription factor Egr-1 is rapidly induced by a variety of stimuli and regulates gene expression through the binding site C-G-C-C-C-C/G-C-G-C (Christy and Nathans, *Mol. Cell. Biol.* 9:4889 (1989)). The sequence C-G-C-C-C-G-C-G-C, which is located at positions -44 to -36 of the 5' untranslated region of the bax promoter (SEQ ID NO: 1; see FIG. 1), can be an Egr-1 regulatory element. Because this inducible transcription factor can be involved in apoptosis (see, for example, Muthukkumar et al., *Mol. Cell. Biol.* 15:6262–6272 (1995), the presence of an Egr-1 regulatory element in the bax promoter indicates that Egr-1 can modulate apoptosis by regulating bax gene expression.

Regulatory elements related to the consensus binding site for the transactivating factor NF-IL-6 (T-G/T-N-N-G-N-A-A-G/T); Combates et al., *J. Biol. Chem.* 269:47 (1994), which is incorporated herein by reference) also are present in the bax promoter at positions -2886 to -2878; -2087 to -2079 and positions -1178 to -1170 of FIG. 1 (SEQ ID NO: 1). IL-6 is a cytokine that can promote cell survival by suppressing apoptosis (Schwarze and Hawley, *Canc. Res.* 55:2262–2265 (1995)) and can down-regulate bax gene expression (see, for example, Lotem and Sachs, *Cell Growth Diff.* 6:647–653 (1995)). The presence of regulatory elements for NF-IL-6 in the bax promoter indicates that NF-IL-6 can suppress apoptosis by directly binding the bax promoter to down-regulate of expression of the bax gene.

Responsive elements for other transcription factors also are present in the bax promoter sequence disclosed herein. For example, additional responsive elements in the bax promoter (SEQ ID NO: 1) include binding sites for Oct-1 (-3604 to -3597); Ets-1 (-3608 to -3601); PEA3 (-3591 to -3586; -2258 to -2253; -1662 to -1657; and -582 to -577); MyoD (-2310 to -2305 and -1825 to -1820); Pit-1 (-1459 to -1452) and half-sites for the estrogen receptor (-2533 to -2529; -2265 to -2261; -1922 to -1918; -1328 to -1324; and -150 to -146); and binding sites for CACGTG binding proteins such as MyoD (-192 to -187; -147 to -142; -99 to -94; and -68 to -63) as indicated in FIG. 1. Such responsive elements also can be important for bax gene expression.

A proximal fragment of the bax promoter has been described (Miyashita and Reed, *Cell* 80:293–299 (1995)). However, this fragment (shown as positions -973 to -1 in FIG. 1) lacks many of the distal regulatory elements contained in the entire bax promoter sequence as disclosed herein (SEQ ID NO: 1). The present invention provides approximately 3.8 kb of bax promoter sequence, including a variety of regulatory elements contained therein. The disclosed entire bax promoter (SEQ ID NO: 1) contains the full complement of regulatory elements involved in regulating expression of the endogenous bax gene in vivo and, therefore, can be particularly useful for identifying agents that regulate expression of a gene operably linked to a bax promoter or an active fragment thereof.

The invention also provides a substantially purified active fragment of a bax promoter. As used herein, an "active fragment of a bax promoter" means a nucleic acid molecule having at least 15 nucleotides of the entire bax promoter (SEQ ID NO: 1), including at least one nucleotide of the nucleotide sequence shown as positions -3885 to -974 in FIG. 1 (SEQ ID NO: 1). An active fragment of a bax promoter is characterized, in part, in that it can confer regulatory activity upon an operably linked nucleic acid molecule. Such an active fragment of a bax promoter can have, for example, 15, 18, 20, 25 or 30 or more nucleotides of SEQ ID NO: 1, including at least one nucleotide of the nucleotide sequence shown as positions -3885 to -974 of SEQ ID NO: 1. In addition, it should be recognized that an active fragment of a bax promoter, which includes at least one nucleotide of the nucleotide sequence shown as positions -3885 to -974 of SEQ ID NO: 1, can include, if desired, two, four, six, ten, twenty or thirty or more nucleotides, for example, of the nucleotide sequence shown as positions -3885 to -974 of SEQ ID NO: 1.

In view of the definition of an active fragment of a bax promoter, it should be recognized, for example, that a portion of a bax promoter having only the sequence shown as positions -973 to -1 in FIG. 1 (SEQ ID NO: 1), is not an active fragment of a bax promoter because it does not contain at least one nucleotide of the sequence shown as positions -3885 to -974 in FIG. 1. However, a portion of a bax promoter having the sequence shown as positions -1178 to -1 in FIG. 1 (SEQ ID NO: 1), which includes an NF-IL-6 responsive element in addition to a p53-RE, contains at least one nucleotide of the sequence shown as positions -3885 to -974 and, thus, is considered an active fragment of a bax promoter, provided that the fragment confers regulatory activity upon an operably linked nucleic acid molecule. Similarly, a portion of a bax promoter having the sequence shown as positions -974 to -1 in FIG. 1 (SEQ ID NO: 1) can be an active fragment of a bax promoter as defined herein, provided that this fragment can confer regulatory activity upon an operably linked nucleic acid molecule.

A particularly useful active fragment of a bax promoter is a nucleic acid molecule having at least 15 nucleotides of SEQ ID NO: 1 that includes at least one nucleotide of the sequence shown as -3885 to -974 in FIG. 1 and that contains one or more of the regulatory elements shown. A particularly useful active fragment of a bax promoter can contain, for example, a p53, Myc, c-Myb, v-Myb, Oct-1, Ets-1, PEA3, NF-IL-6, estrogen receptor, MyoD, AP-1, Pit-1, NF-κB or Egr-1 regulatory element, or combination thereof, as disclosed herein (see FIG. 1. An active fragment of a bax promoter containing, for example, at least 25 or 30 nucleotides of SEQ ID NO: 1 is particularly useful in that it can contain a combination of two such regulatory elements.

Methods such as those disclosed herein or otherwise known in the art can be used to identify an active fragment of a bax promoter, which confers regulatory activity upon a linked gene. For example, deletion mutants of the entire bax promoter (SEQ ID NO: 1) can be constructed and the remaining portion analyzed for the ability to confer regulatory activity upon a linked gene. Methods for preparing a portion of the bax promoter (SEQ ID NO: 1), such as a 5' or 3' deletion or an internal deletion are well known in the art, and include, for example, the use of naturally occurring or engineered restriction sites, nuclease digestion or oligonucleotide-directed "loop-out" mutagenesis (see Sambrook et al., *Molecular Cloning: A Laboratory Manual*, Cold Spring Harbor Laboratory Press (1989), which is incorporated herein by reference). In addition, a small portion of the bax promoter can be constructed by annealing complementary synthetic oligonucleotides (see Example II.B).

A portion of the entire bax promoter sequence (SEQ ID NO: 1) can be assayed for the ability to confer regulatory activity by analyzing, for example, expression of an operably reporter gene in a transient transfection assay, as is well known in the art. In order to identify an active fragment of a bax promoter, a chloramphenicol acetyl transferase (CAT) reporter gene, for example, can be linked to various portions of the bax promoter and assayed for regulatory activity as described in Example II.C. A portion of the bax promoter also can be assayed for regulatory activity using, for example, a luciferase or a β-galactosidase reporter gene. These and other reporter genes are well known in the art (Sambrook, supra, 1989) and are commercially available.

The bax promoter, or an active fragment thereof, also can be modified to contain nucleotide substitutions, additions or deletions that do not alter the ability of the sequence to confer regulatory activity upon a linked gene. A point mutation can be introduced into the bax promoter or an active fragment thereof using, for example, site-directed mutagenesis (see Example II.B. or Wu (ed.), *Meth. in Enzymol.*, Vol. 217, San Diego: Academic Press (1993), incorporated herein by reference) or by synthesizing a sequence having random nucleotides at one or more predetermined positions. Methods of testing a modified bax promoter, or an active fragment thereof, for the ability to confer regulatory activity upon a linked gene are well known in the art. A modified bax promoter or modified active fragment thereof containing a modification that does not alter its ability to confer regulatory activity on a linked gene is encompassed within the meaning of "bax promoter" or "active fragment of a bax promoter," respectively, as used herein.

The term regulatory activity, as used herein, means constitutive or regulated transcriptional activity that is conferred upon an operably linked nucleic acid molecule under appropriate conditions. The regulatory activity of an active fragment of a bax promoter, for example, is transcriptional activity that is conferred upon a linked reporter gene under appropriate conditions, as compared to the transcriptional activity of the reporter gene in the absence of the active fragment. Appropriate conditions can include, for example, the cell type in which the regulatory activity is assayed and the conditions in which the cells are grown, including, for example, the serum or growth factors present in the medium. Appropriate conditions generally are determined by the presence or absence of the particular transcription factors influencing the regulatory activity of the bax promoter and whether these factors are active or inactive due, for example, to mutations or post-translational modifications.

Appropriate conditions for demonstrating the regulatory activity of an active fragment of a bax promoter having a p53-RE, for example, include a cell type containing p53 protein such as cell line having endogenous wild type p53 or a p53-null cell line transfected with a p53 expression vector. Under such conditions, regulatory activity can be conferred, as indicated by the differential activity of a reporter gene construct containing the active fragment having a p53-RE as compared to a reporter gene construct lacking the active fragment of the bax promoter.

The invention also provides a nucleic acid molecule containing a nucleotide sequence encoding a gene product operably linked to a bax promoter. The invention provides, for example, a nucleic acid molecule having a nucleotide sequence encoding a gene product operably linked to the nucleotide sequence shown as positions -3885 to -1 of FIG. 1 (SEQ ID NO: 1). The invention also provides a nucleic acid molecule having a nucleotide sequence encoding a gene product operably linked to the nucleotide sequence shown as positions -3885 to -974 of (SEQ ID NO: 1). A useful nucleotide sequence encoding a gene product can be, for example, a reporter gene such as luciferase, β-galactosidase, chloramphenicol acetyl transferase or green fluorescent protein; a selectable marker such as thymidine kinase, dihydrofolate reductase, aminoglycoside phosphotransferase or hygromycin B phosphotransferase; or a toxin such as ricin.

The term "linked" is used herein its broadest sense and indicates that a nucleotide sequence encoding a gene product and a bax promoter or an active fragment thereof, for example, are located within a continuous DNA sequence that usually does not exceed about ten to fifty kilobases (kb). The term "operably linked," when used in reference to a nucleotide sequence encoding a gene product and a bax promoter or an active fragment thereof, means that a nucleotide sequence, which can encode a gene product, is linked to the bax promoter such that the bax promoter regulates expression of the gene product under appropriate conditions. Two nucleotide sequences that are operably linked contain elements essential for transcription, including, for example, a TATA box. One skilled in the art knows, for example, that an active fragment of a bax promoter that lacks minimal promoter elements can be operably linked to a reporter plasmid containing a minimal promoter such as the minimal promoter CAT reporter plasmid pA10-CATBS described in Example II.B.

Dysregulated bax expression can be involved in a variety of diseases that are characterized by an abnormal level of cell death. The isolation of the entire bax promoter (SEQ ID NO: 1) and the availability of a variety of cell types from patients having diseases characterized by an abnormal level of cell death allow for the identification of agents that can regulate the level of bax gene expression, and, therefore, can be useful to effectively treat such patients. Thus, the invention also provides screening assays for identifying an effective agent such as a drug that regulates the level of expression of a gene operably linked to a bax promoter.

An agent that effectively regulates the level of expression in a cell of a gene operably linked to a bax promoter or an active fragment thereof can be identified, for example, by introducing into the cell a nucleic acid molecule containing the gene operably linked to the bax promoter or the active fragment thereof; determining a control level of expression of the gene in a cell containing the gene; contacting a cell containing the gene with an agent suspected of being an effective agent; and determining a test level of expression of the gene in the cell contacted with the agent, where a difference in the test level of expression as compared to the control level of expression identifies the agent as an effective agent.

The invention provides, for example, a method of identifying an effective agent that reduces or inhibits the level of expression in a cell of a gene operably linked to a bax promoter or an active fragment thereof. Such an effective agent can be identified, for example, using a p53-deficient cell or using a cell that expresses a p53 tumor suppressor such as a neuron or lymphocyte. The invention also provides a method of identifying an effective agent that increases the level of expression in a cell of a gene operably linked to a bax promoter or an active fragment thereof. A useful cell for such methods can be, for example, a p53-deficient cell such as a p53 null cell; a cell that expresses a mutant p53 tumor suppressor; or a cell that expresses a p53 tumor suppressor, for example, a tumor cell.

As used herein, the term "agent" means a biological or chemical compound such as a simple or complex organic molecule, a peptide, a protein or an oligonucleotide. The screening assays described herein are particularly useful in that they can be automated, facilitating high through-put screening of randomly or rationally designed agents in order to identify those agents that effectively regulate the level of expression in a cell of a gene operably linked to a bax promoter or an active fragment thereof. Thus, the screening assays disclosed herein provide a method of identifying an "effective agent," which is useful to modulate cell death in a cell in vitro or in a patient as described below.

As used herein, the term "test level of expression," means a level of expression of a gene operably linked to a bax promoter or an active fragment thereof that is assayed in a cell that has been contacted with an agent suspected of being an effective agent. The term "control level of expression," as used herein, means a level of expression of a gene operably linked to a bax promoter or an active fragment thereof that is assayed in a cell that has not been contacted with an agent suspected of being an effective agent. The cell in which the control level of expression is determined can be the same cell in which the test level of expression is determined, provided that the control level of expression is determined prior to contacting the cell with the agent. In addition, a control level of expression can be determined in a different cell, into which a nucleic acid molecule containing a gene operably linked to a bax promoter or an active fragment thereof has been introduced. To determine a control level in a different cell, one skilled in the art knows that the cell that is not contacted with the agent is cultured under the same conditions as the cell contacted with the agent. Furthermore, it is recognized that a determining a control level of expression of a gene operably linked to a particular bax promoter or an active fragment thereof can entail assaying the level of expression in a cell of a gene operably linked to a particular bax promoter or an active fragment thereof or can entail, for example, referencing historical values of the level of expression in a cell of a gene operably linked to the particular bax promoter or an active fragment thereof.

The term "different," as used herein, means that, upon comparison of a test level of expression and a control level of expression, there is a difference in the test level of expression and the control level of expression that is not within the inherent variability of the particular assay used to determine the levels of expression.

An effective agent identified according to a method of the invention can modulate the level of apoptosis in a cell by increasing or decreasing the level of expression of a bax gene. An effective agent for treating cells characterized by an abnormally high level of cell death, for example, can reduce or inhibit bax gene expression and, thereby, decrease apoptosis in the cell. Although no mechanism is proposed, such an effective agent can act in a variety of ways. An effective agent for reducing or inhibiting bax gene expression can be, for example, an oligonucleotide that competes for binding to a transcription factor, such as Myc, Myb, Jun, NF-κB or p53, that normally binds and up-regulates expression of a bax gene. For example, an effective agent can have the structure of a Myb responsive element and can bind free Myb in a cell, thus preventing Myb from up-regulating expression of the gene in its normal fashion. An effective agent also can bind to the DNA binding domain of Myb, or another transcription factor that normally functions to up-regulate bax gene expression, or to the Myb responsive element in order to sterically inhibit binding of Myb to the Myb responsive element. An effective agent for reducing or inhibiting bax gene expression also can be, for example, a peptide or protein that binds to a response element and acts as a surrogate for a transcription factor, such as NF-IL-6, that normally functions to decrease bax gene expression.

In contrast, an effective agent for treating a disease characterized by an abnormally low level of cell death can increase bax gene expression in a cell. An effective agent for treating a cancer cell, for example, can increase bax gene expression, thereby promoting apoptosis in the cancer cell. Such an effective agent can act in a variety of ways. For example, an effective agent that is a peptide or a protein can increase bax gene expression by binding to a responsive element that normally mediates up-regulation of bax expression, such as a Myc, Myb, Jun, NF-κB or p53 responsive element, and increasing expression of the bax gene. In a cell expressing a mutant p53 protein, an effective agent also can be a small organic molecule that alters the structure or binding ability of the mutant p53 protein such that the mutant p53 can bind to a p53-RE and increase bax gene expression in the absence of wild type p53. Alternatively, an effective agent for increasing bax gene expression can be an oligonucleotide that competes for binding to a transcription factor that normally binds and down-regulates expression of a bax gene, for example NF-IL-6, such that the factor is prevented from down-regulating bax expression in its normal manner.

A transfection assay can be a particularly useful screening assay for identifying an effective agent as shown in Example III.B. In a transfection assay, a nucleic acid containing a gene such as a reporter gene that is operably linked to a bax promoter, or an active fragment thereof, is transfected into the desired cell type. A test level of reporter gene expression is assayed in the presence of an agent suspected of being an effective agent and compared to a control level of expression. An effective agent is identified as an agent that results in a test level of expression that is different than a control level of reporter gene expression, which is the level of expression determined in the absence of the agent. Methods for transfecting cells and a variety of convenient reporter genes are well known in the art (see, for example, Goeddel (ed.), Meth. in Enzymol., Vol. 185, San Diego: Academic Press, Inc. (1990), incorporated herein by reference; see, also, Sambrook, supra, 1989).

As used herein, the term "reporter gene" means a gene encoding a gene product that can be identified using simple, inexpensive methods or reagents and that can be operably linked to a bax promoter or an active fragment thereof. As exemplified below, the chloramphenicol acetyltransferase reporter gene can be used to determine transcriptional activity. Other reporter genes such as a luciferase, β-galactosidase or green fluorescent protein reporter gene, for example, also can be used in the screening assays of the invention (see Sambrook, supra, 1989).

A cotransfection assay also can be particularly useful in the screening methods of the invention (see Example III). A cotransfection assay provides a well-defined system containing, for example, an inducible transcription factor and a reporter gene that is operably linked to a bax promoter or an active fragment thereof. For example, a bax promoter or active fragment thereof containing a p53-RE can be cotransfected with an inducible p53 tumor suppressor such as a temperature-sensitive p53 tumor suppressor (see Example III.A; see, also, Miyashita et al., supra, 1994a, and Sakamuro et al., *Oncogene* 11 2411–2418 (1995), which is incorporated by reference herein). Following cotransfection, agents can be screened at the non-permissive temperature to identify an effective agent, which will modulate transcription from the p53-RE to the same extent as the p53 protein does when expressed at the permissive temperature. Such a system contains a well-defined standard with which to compare the screening results.

An inducible transcription factor useful in a screening method of the invention also can be a steroid inducible transcription factor. For example, when a transcription factor, such as Myc, Myb, Fos, Jun or MyoD, is fused to the ligand binding domain of the estrogen receptor, the activity of the transcription factor is rendered dependent on the presence of estrogen or an estrogen agonist (see, for example, Eilers et al., *Nature* 340:66–68 (1989); Littlewood et al., *Nucl. Acids Res.* 23:1686–1690 (1995); Lyon and Watson, *Differentiation* 59:171–178 (1995); Preston et al., *Mol. Cell. Biol.* 16:211–218 (1996); Fialka et al., *J. Cell. Biol.* 132:1115–1132 (1996); and Hollenberg et al., *Proc. Natl. Acad. Sci. USA* 90:8028–8032 (1993), each of which is incorporated herein by reference). A cell cotransfected with a nucleic acid molecule encoding a chimeric protein containing Myc, Myb or Jun, for example, fused to an estrogen receptor ligand binding domain and an active fragment of a bax promoter that includes a corresponding Myc, Myb or AP-1 response element can be particularly useful in a screening method of the invention. In such a cotransfected cell, an agent can be screened in the absence of estrogen to identify an effective agent, which will modulate transcription from the corresponding response element to the same extent as the inducible Myc, Myb or Jun in the presence of estrogen. One skilled in the art knows that these and other inducible transcription factors that regulate a bax promoter or active fragment thereof, including temperature-sensitive and steroid inducible variants of p53, Myc, Myb, NF-KB, AP-1, Egr-1 and NF-IL-6, can be useful in identifying an effective agent according to the screening methods disclosed herein.

A screening method of the invention can be practiced with a variety of cell types. A particularly useful cell type is a cell characterized by an abnormal level of cell death. Such a cell can be obtained from the American Tissue Type Culture and exhibits the characteristics of a cell obtained from a patient having a disease characterized by an abnormal level of cell death. Such a cell line can be a cell line derived from a patient with ataxia telangiectasia or a neuronal cell line treated with amyloid beta protein (ABP) or glutamate that is useful as a model of the cell death that occurs in Alzheimer's disease or stroke, respectively (Behl et al., *Biochem. Biophys. Res. Comm.* 197:949–956 (1993), which is incorporated herein by reference). A particularly useful cell line also can be derived from a patient having a disease characterized by an abnormal level of cell death such as cancer.

A cell line obtained, for example, from a cancer patient can be particularly useful in practicing a method of the invention. Using such a cell line, a reporter gene operably linked to a bax promoter or an active fragment thereof can be used to identify an effective agent that regulates the level of expression of a gene operably linked to a bax promoter or an active fragment thereof. As described in Example III.B., a cotransfection assay using a cancer patient-derived cell line can be useful for identifying an agent that increases the level of expression of a gene operably linked to a bax promoter or an active fragment thereof. Such an assay allows the identification of an agent that can be particularly effective at increasing endogenous bax gene expression and, therefore, at promoting apoptosis in the cancerous cells of the particular patient.

A gel shift assay also can be used to identify an effective agent that regulates the level of expression of a gene operably linked to a bax promoter or an active fragment thereof. A gel shift assay is particularly useful because it does not require the use of living cells. For example, a gel shift assay can be used as a primary method of screening for potentially effective agents, which can then be examined using a transfection method as described above (see Example IV). Using a fragment of a bax promoter as a probe, binding reactions are performed with the desired transcription factors, which can be recombinant or purified factors, or cell extracts prepared from a desired cell type. For example, the binding of in vitro translated p53 to the 37 bp fragment of the bax promoter containing a p53-RE (SEQ ID NO: 2) is described in Example II.D. Similarly, sources of recombinant transcription factors such as Myc, Myb, NF-KB, AP-1, Egr-1 and NF-IL-6, for example, or cell types containing these factors, are known in the art and can be used in a gel shift assay to identify an effective agent that regulates the level of expression of a gene operably linked to a bax promoter or an active fragment thereof.

A gel shift assay can be automated, allowing for the rapid screening of a large number of potentially effective agents. For example, binding reactions can be performed in 96 well plates, where each well contains a similar binding reaction mixtures to which is added an agent to be screened. Following incubation of the binding reactions, the samples can be transferred in parallel to precast gels for separation of the reaction products. An effective agent can be identified by its ability to increase or decrease specific binding of a regulating factor to the probe, which is a fragment of a bax promoter.

The bax promoter (SEQ ID NO: 1) shown in FIG. 1, or an active fragment thereof, is useful in the screening assays of the invention. As discussed above, the entire bax promoter sequence (SEQ ID NO: 1) contains the full complement of regulatory elements involved in regulating expression of an endogenous bax gene in vivo, and, therefore, provides an advantage over the smaller fragment of the bax promoter previously described. For example, the entire bax promoter sequence (SEQ ID NO: 1) contains a proximal p53-RE at nucleotides -485 to -449 as well as a distal p53-RE at nucleotides -2724 to -2697. Synergistic transcriptional activation involving a combination of proximal and distal p53 binding sites, with looping out of the intervening DNA, has been described previously (Stenger et al., *EMBO J.* 13:6011–6020 (1994), which is incorporated herein by reference). Thus, a p53 tetramer bound at a proximal p53-RE of the bax promoter can interact with a p53 tetramer bound at a distal p53 of the bax promoter to synergistically activate transcription. In view of cooperativity between widely separated p53 binding sites, the entire bax promoter sequence (SEQ ID NO: 1) or an active fragment thereof containing two or more p53-RE's, such as an active fragment containing the sequence from -2724 to -449 of SEQ ID NO: 1, can be particularly useful in a screening assay of the invention.

Furthermore, the entire bax promoter (SEQ ID NO: 1) contains regulatory elements that are not present in the previously described -973 to -1 fragment of the bax promoter, such as regulatory elements for Myb, AP-1 and NF-IL-6. Therefore, the entire bax promoter (SEQ ID NO: 1), or an active fragment thereof containing a regulatory element for Myb, AP-1 or NF-IL-6, for example, can be useful for conferring Myb, AP-1 or NF-IL-6 regulatory activity, respectively, on a linked gene and for identifying an effective agent that regulates the level of bax gene expression through one of these regulatory elements. Thus, the novel bax promoter sequence (SEQ ID NO: 1), which contains a wide variety of regulatory elements, including regulatory elements not present in the previously described proximal fragment of the bax promoter, can be used to identify a wide variety of agents that effectively regulate the level of expression of a gene operably linked to a bax promoter or an active fragment thereof, such as a bax gene.

Complex promoters such as the bax promoter generally act through the combination of two or more regulatory elements, which can produce a coordinate regulatory activity that is distinct from the activity conferred by a single element. Such cooperative interactions between transcription factors that bind to two or more regulatory elements are well known in the art to be important in determining gene regulatory activity. A direct physical association, for example, can be involved between different transcription factors, and such cooperatively acting factors can more tightly regulate, for example, the process of transcription initiation. For example, the p53 tumor suppressor, which binds to the p53-RE (SEQ ID NO: 2) located at positions -485 to -449 of the bax promoter, can cooperate with a transcription factor binding to a regulatory element contained within the distal region of the bax promoter (positions -3885 to -974 of SEQ ID NO: 1) to produce a unique gene regulatory activity. Thus, an active fragment of a bax promoter containing a regulatory element in addition to a p53-RE can be particularly useful in identifying an effective agent that regulates the level of expression in a cell of a gene operably linked to a bax promoter or an active fragment thereof.

Use of the entire bax promoter (SEQ ID NO: 1) allows identification of an effective agent that regulates expression of a gene operably linked to a bax promoter or an active fragment thereof. Such an agent can be useful to modulate the level of apoptosis in a disease that is characterized by an abnormal level of cell death. In such a disease, the level of apoptosis in an affected cell is different than the level of apoptosis in a corresponding normal cell. An example of a disease characterized by an abnormal level of apoptosis is cancer, in which the level of apoptosis in the cancerous cell is reduced as compared with the level of apoptosis in a normal cell of the type from which the tumor cell was derived. Thus, an effective agent identified according to a method of the invention can be useful in modulating the level of apoptosis in a cell.

An effective agent identified according to the methods of the invention is useful for reducing or inhibiting the level of bax gene expression. For example, an effective agent that reduces or inhibits bax gene expression can be used to treat a patient having a disease characterized by an abnormally high level of apoptosis. An effective agent that reduces or inhibits bax gene expression also can be useful in reducing or preventing the death of normal cells in a patient receiving therapy, such as chemotherapy or radiation therapy.

An effective agent identified according to the methods of the invention can be useful for treating a disease characterized by an abnormally high level of cell death such as stroke. In stroke, oxygen deprivation leads to necrotic cell death. Subsequent destruction of necrotic neuronal cells leads to release of agents such as glutamate, which can induce apoptosis in surrounding cells presumably, in part, by allowing intracellular levels of active oxygen species to increase (Behl, supra, 1993). Bax can be involved in the apoptosis subsequent to ischemia since Bax protein levels are upregulated in neurons of adult rat brain following cerebral ischemia (Krajewski et al., *J. Neurosci.* 15:6364–6376 (1995), which is incorporated herein by reference). Ischemia induced high levels of Bax protein in some populations of neurons that are particularly sensitive to cell death induced by transient global ischemia. In addition, postischemic elevations of Bax protein were detected in neurons with the DNA-breaks indicative of apoptosis, further strengthening the association of Bax and apoptosis in the context of ischemia (Krajewski et al., supra, 1995).

Alzheimer's disease, ataxia telangiectasia, Bloom's syndrome and progeria, for example, also are characterized by having an abnormally high level of cell death and can be treated using an effective agent identified according to a method of the invention. Such a disease is characterized by an accumulation of DNA damage due, for example, to oxidative damage or to defects in DNA repair. For example, cells from ataxia telangiectasia patients are highly susceptible to ultraviolet- and X-radiation, which damages DNA in the cells and induces apoptosis. Furthermore, exposure of ataxia telangiectasia cells to radiation results in increased expression of genes containing a consensus p53 binding site (Kastan et al., *Cell* 71:587–597 (1992), which is incorporated herein by reference). Therefore, abnormalities in cell death regulation in ataxia telangiectasia patients can be due to a defect in p53-mediated regulation of a bax gene.

An effective agent that increases bax gene expression also can be identified according to the methods of the invention and can be used to increase apoptosis in a cell. For example, a cancer patient can be treated by administering an effective agent that was identified according to a method of the invention as increasing the level of expression in a tumor cell of a gene operably linked to a bax promoter or an active fragment thereof.

The importance of the regulation of apoptosis for in vivo suppression of tumor formation by p53 has been demonstrated in studies using transgenic mice. In these mice, tumor development was associated with the loss of p53 and was characterized by a decreased rate of cell death rather than by an increased rate of cell proliferation (Symonds et al., *Cell* 78:703–711 (1994)). Furthermore, the relative insensitivity of p53-deficient tumor cells to the induction of apoptosis by chemotherapeutic drugs and radiation may be responsible for the clinical observation that patients having p53-deficient tumor cells tend to have a worse prognosis than patients having histologically similar tumors that contain normal p53 (see, for example, Thor et al., *J. Natl. Canc. Inst.* 84:845–855 (1992); Sun et al., *Lancet* 340:1369–1373 (1992)).

The p53 tumor suppressor often is absent or mutated in cancer cells. As a result, bax gene expression can be improperly regulated in the p53-deficient cancer cells, resulting in a lower than normal level of Bax protein and a corresponding decrease in the level of apoptosis in these cells. As used herein, the term "p53-deficient cell" is meant to include any cell that does not express wild-type p53 tumor suppressor protein. Such a cell, for example, can be a p53-null cell, which is a cell that does not contain any p53 protein, or a cell that contains a mutant p53 protein. A cancer cell that has point mutations, allelic loss, rearrangements or deletions of both p53 genes and, therefore, either does not express a p53 protein or expresses only mutant p53 protein is an example of a p53-deficient cell. A number of p53-deficient cells are known and include, for example, H358 lung cancer-derived cells and Saos-2 osteosarcoma cells, which are described in Examples II and III. Such cells are particularly useful for identifying agents that can effectively regulate cell death (see Examples II and III).

Although the primary defect in a patient's cancer cell that results in improper bax expression may be a deficiency in p53, it is recognized that an effective agent for treating such a patient can modulate bax gene expression through a variety of mechanisms. For example, such an agent can restore the deficient p53-mediated regulation, thereby increasing bax gene expression. In addition, such an effective agent can increase bax expression through another responsive element such as a Myc, Myb, AP-1 or NF-κB responsive element disclosed herein.

The following examples are intended to illustrate but not limit the present invention.

EXAMPLE I

The p53 Tumor Suppressor Induces Apoptosis by Modulating the Level of Expression of Bax This example demonstrates that the p53 tumor suppressor acts as a transcription factor that increases bax gene expression, thereby inducing apoptosis in a cell.

A. Transfection of M1 cells with a plasmid encoding a temperature-sensitive p53 tumor suppressor Cells from the murine myeloid leukemic cell line, M1, which do not express either the p53 tumor suppressor protein or mRNA encoding p53 (Yonish-Rouach et al., supra, 1991), were maintained in Dulbecco's Modified Eagle's Medium (DMEM) supplemented with 10% (vol/vol) heat-inactivated horse serum, 2 mM glutamine, 50 U/ml penicillin and 0.1 mg/ml of streptomycin. Cells were either transfected with pSV2-Neo, alone, or were cotransfected with pSV2-Neo and pLTRp53cGval135, which encodes the murine Val-135 mutant p53, (see Michalovitz et al., *Cell* 62:671-680 (1990), which is incorporated herein by reference). The p53 tumor suppressor encoded by the plasmid, pLTRp53cGval135, is a temperature-sensitive mutant that has normal p53 activity at the permissive temperature, 32.5° C., but is inactive at the non-permissive temperature, 37° C. Transfection was by electroporation using the BioRad Gene Pulser (Biorad, Hercule, Calif.). A pulse (1.5 kV, 1 mF) was delivered to a 0.7 ml suspension containing 1.5×107 cells and 50 μg of linearized plasmid DNA.

Following transfection, the cells were transferred into 24 well tissue culture plates at a concentration of 5×10$^4$ cells per well and allowed to adjust to the culture medium. After 48 hr incubation, the medium was removed and replaced with fresh medium containing 400 μg/ml of geneticin (1 ml per well; GIBCO/BRL, Gaithersburg, Md.). In the cotransfected cells, one drug resistant clone, designated M1-p53, that expressed the highest levels of p53 was selected and used for further experiments. In the parallel transfection, one cell line, designated M1-Neo, was selected and used as a control in further studies.

B. Effect of p53 tumor suppressor on cell survival

M1-p53 and M1-Neo cells were incubated at either 32.5° C. or 37.5° C. Cell samples were taken at various times and viability was determined by trypan-blue exclusion (mean ± standard deviation for three experiments). Shifting the M1-p53 cells to 32.5° C., which is the permissive temperature, resulted in cell death. Since a large number of M1-p53 cells die following incubation for 19 hr at 32.5° C., prior to some experiments dead cells were removed by centrifugation in "HISTOPAQUE"™ (Sigma, St. Louis, Mo.) as described by the manufacturer. In contrast, cell survival was unchanged in M1-p53 cells maintained at 37° C., which is the non-permissive temperature, and in M1-Neo cells incubated at either 32.5° C. or at 37° C. These results indicate that expression of the p53 tumor suppressor in a cell results in cell death.

C. Effect of p53 tumor suppressor on Bax mRNA levels

The product of the bax gene is involved in the process of apoptosis in a cell. Therefore, the level of bax mRNA expression was determined by northern blot analysis and compared to the level of expression of β2-microglobulin mRNA.

M1-p53 and M1-Neo were incubated at 32.5° C. or 37° C. for various times, then collected. In samples of M1-p53 cells harvested 19 hr after being shifted to 32.5° C., dead cells were removed by centrifugation in "HISTOPAQUE"™ (Sigma). Total RNA was isolated using "TRIZOL"™ reagent (GIBCO/BRL) as described by the manufacturer, and 15 μg total RNA was size-fractionated in 1.2% agarose gels containing 2.2M formaldehyde (Sambrook et al., supra, 1989). RNA was transferred to "GENE SCREEN PLUS"™ nylon filters (NEN Research Products, Boston, Mass.) using 10×SSC (1×SSC=0.15M NaCl/0.015 M sodium citrate) and covalently bound to the membrane using UV irradiation. Probes, as described below, were labelled using α-$^{32}$P-dCTP by the random primer method (Sambrook et al., supra, 1989; specific activity =1×10$^9$ cpm/μg).

$^{32}$P-labelled probes were added to the hybridization solution and hybridization was performed for 16 hr at 42° C. (hybridization solution is 50% formamide, 10% dextran sulfate, 1M NaCl, 1% SDS, 1× Denhardt's solution, 25 mM Tris (pH 7.4) and 50 mg/ml denatured salmon sperm DNA) (50×Denhardt's solution contains 5 g Ficoll (Type 400; Pharmacia, Piscataway, N.J.), 5 g polyvinylpyrrolidone, 5 g bovine serum albumin (Fraction V; Sigma) and water to 500 ml). Following hybridization, the filters were washed with 2×SSC/0.1% SDS at room temperature, then with the same solution at 68° C. and exposed to X-ray film as described above.

A murine bax-specific probe was prepared by amplifying the entire open reading frame of the bax cDNA using RT-PCR. Five μg total RNA was incubated in a 50 μl reaction volume containing 200 units Moloney Leukemia Virus Reverse Transcriptase (GIBCO/BRL), 4 μl random hexamer (62.5 A260 units/ml), 10 mM dithiothreitol, 20 units RNAsin (Promega, Madison, Wis.) and 1 mM each od dGTP, dATp, dTTP and dCTP in the reaction buffer provided by the manufacturer. Reactions were incubated at 37° C. and allowed to proceed for one hour.

The cDNA product was amplified using the PCR method. Ten μl of the cDNA product was resuspended in a 100 μl reaction volume containing 2.5 U Taq DNA polymerase (Perkin-Elmer-Cetus, Foster City, Calif.), 60 mM each of dGTP, dATP, dTTP and dCTP and 50 pmol each of the forward and reverse primers in the reaction buffer provided by the manufacturer (primers are described below). Amplification cycles consisted of 94° C. for 30 sec, 57° C. for 30 sec, 72° C. for 3 min.

The forward primer was 5'-GGAATTCGCGGTGATGGACGGGTCCGG-3'(SEQ ID NO: 4) and the reverse primer was 5'-GGAATTCTCAGCCCATCTTCTTCCAGA-3'(SEQ ID NO: 5). An Eco RI linker sequence was included at the 5'-end of each primer (underlined). Amplified cDNA products were gel-purified using "GENE CLEAN" II™ (Bio 101, Inc., La Jolla, Calif.), cleaved using Eco RI (10 U/μg DNA) and subcloned into a Bluescript plasmid pSK-II (Stratagene, Inc., La Jolla, Calif.). An Eco RI restriction fragment of approximately 600 base pairs was excised from the cloned insert, gel-purified and used as a hybridization probe. The murine μ2-microglobulin cDNA probe is described by Parnes et al., *Proc. Natl. Acad. Sci.. USA* 78:2253–2257 (1081), which is incorporated herein by reference.

When M1-p53 cells were shifted to the permissive temperature, the level of bax mRNA rapidly increased. No change in bax mRNA levels were observed in M1-p53 cells maintained at 37° C. or in M1-Neo cells incubated at either 32.5° C. or at 37° C. Levels of β2-microglobulin mRNA did not change in any of the samples. These results indicate that the p53 tumor suppressor increases the expression of bax mRNA. Thus, the p53 tumor suppressor regulates the expression of the bax gene, which is involved in cell death.

D. Effect of p53 tumor suppressor on Bax protein levels

Increased levels of Bax protein induce apoptosis in a cell. In order to confirm that the mRNA changes described above are responsible for the increased Bax protein level associated with apoptosis, the level of Bax protein was determined.

M1-p53 and M1-Neo were incubated at 32.5° C. or 37° C. for various times, then collected. In samples of M1-p53 cells harvested 19 hr after being shifted to 32.5° C., dead cells were removed by centrifugation in "HISTOPAQUE"™ (Sigma). Cells were washed in ice cold phosphate-buffered saline (PBS; pH 7.4) and collected by centrifugation. The cell pellets were resuspended in ice-cold lysis buffer containing the protease inhibitors, 0.7 mg/ml pepstatin, 1 mM phenylmethylsulfonylfluoride (PMSF), 0.23 U/ml aprotinin, 10 mM leupeptin and 1 mM benzamidine (lysis buffer is 10 mM Tris (pH7.4), 0.15 M NaCl, 5 mM EDTA, 1% (v/v) Triton X-100). Following incubation on ice for 30 min, samples were centrifuged at 16,000×g for 10 min and the postnuclear supernatants were collected. Protein concentrations were determined using the bicinchoninic acid protein assay kit (Pierce, Inc., Rockford, Ill.).

Twenty µg protein were size-fractionated under reducing conditions by sodium dodecyl sulfate-polyacrylamide gel electrophoresis (SDS-PAGE) using 12% gels, as described by Laemmli et al. (*Nature* 227:68014 685 (1970), which is incorporated herein by reference), then electrophoretically transferred to nitrocellulose filters. The filters were incubated for 2 hr at room temperature with preblocking solution (10 mM Tris (pH 7.6), 0.15M NaCl, 5% skim milk, 2% BSA and 0.1% Tween 20), then the solution was removed, fresh solution containing 0.1–0.2% (vol:vol) of the appropriate antibody (described below) was added and incubation was continued for 16 hr at 4° C.

Following incubation with the first antibodies, the filters were washed 3×(5 min each) in a solution containing 0.12M NaCl, 8.7 mM NaH$_2$PO$_4$, 31 mM K$_2$HPO$_4$ (pH 7.6), then incubated with preblocking solution for 30 min, followed by fresh preblocking solution containing biotinylated goat anti-rabbit IgG (H+L) antibody (Vector Laboratories, Inc., Burlingame, Calif.). After washing as above, antibody binding was detected using an avidin-biotin-complex method, which employed the Vectastain ABC kit (Vector Laboratories Inc.) followed by the addition of 0.4 mg/ml AEC (3-amino-9-ethyl carbazole) containing 0.01% H$_2$ O$_2$ for color development.

Rabbit anti-mouse Bax antibody was raised against a synthetic peptide corresponding to amino acids 43 to 61 of the mouse Bax protein, including an additional cysteine at the N-terminus (CPELTLEQPPQDASTKKLSE; SEQ ID NO: 6), conjugated to maleimide-activated Keyhole Limpet Hemocyanin (Pierce, Inc.).

The steady-state level of the p20-Bax protein increased following the shift of M1-p53 cells to the permissive temperature. These results indicate that induction of apoptosis by the p53 tumor suppressor is achieved by p53-regulation of the transcriptional activity of the bax gene. Furthermore, the magnitude of the effect shown here likely is an underestimate of the actual change in the level of Bax expression, since cells with low high Bax levels undergo apoptosis and, therefore, are lost from the population of cells analyzed in these experiments.

EXAMPLE II

Characterization of the bax promoter

This example describes a method for identifying and characterizing the bax promoter.

A. Library screening

This section describes the construction and screening of a human genomic DNA library.

A human placental DNA library was cloned into the cosmid vector pWE15 (Stratagene, Inc.) and was screened by a colony hybridization procedure using "BIODYNE™" nylon membranes (Pall Support Division, East Hills, N.Y.) and a $^{32}$P-labelled mouse bax cDNA (Miyashita et al., supra, 1994a). Filters were hybridized for 16 hr at 65° C. with $10^6$ cpm/ml bax cDNA probe in 6×SSC containing 0.5% SDS, 5×Denhardt's solution and 100 µg denatured salmon sperm DNA. Following hybridization, filters were washed in 2×SSC/0.1% SDS, twice at 25° C., then once at 65° C.

Approximately 4×10$^5$ colonies were screened. Positive colonies were selected and rescreened. After three rounds of screening, 8 colonies remained positive. The cloned DNA in the positive colonies was examined by restriction endonuclease mapping and found to represent three independent, overlapping genomic clones that were designated pTM597-1, 2, and 4.

pTM597-2 was digested with Bam HI to produce one fragment of approximately 4 kb and two fragments of about 3 kb, which were subcloned into Bluescript pSKII (Stratagene, Inc.) to generate the plasmids pTM604-4, pTM604-6 and pTM604-7, respectively. The approximately 4 kb Bam HI fragment of pTM597-2 contains the entire bax promoter provided as nucleotides -3885 to -1 in FIG. 1 (SEQ ID NO: 1).

A TATAA box is located 398 bp upstream from the open reading frame in the human bax gene. A transcription start site was mapped by primer extension to a position approximately 22 bp downstream of the TATAA box. Thus, the 5'-UTR of the human bax gene is predicted to be about 370 bp in length (see FIG. 1).

A p53 binding site consists of two copies of the 10 bp motif 5'-Pu-Pu-Pu-C-(A/T)-(T/A)-G-Py-Py-Py-3'(SEQ ID NO: 3; Pu=purine; Py=pyrimidine) separated by 0 to 13 bp (El-Deiry et al., supra, (1992)). Inspection of the bax promoter revealed a perfect p53 binding site (10/10 matches with consensus sequence) and three imperfect p53 binding sites located upstream of the TATAA box at positions -485 to -449 (see FIG. 1).

In the bax promoter, the perfect 10 bp consensus site (-474 bp to -465 bp) is flanked on the 5'-side by a sequence that shares 7 of 10 matches with the consensus sequence, including a stretch of 7 of 7 matches in the core of this motif (FIG. 1). This second potential p53 binding site is separated from the perfect site by a single nucleotide. On the 3'-side of the perfect consensus site are two additional imperfect 10 bp motifs that are separated from the perfect p53 binding site by 0 or 6 bp and have 7/10 or 8/10 matches, respectively, with the consensus sequence.

Also within the 5'-UTR of the bax promoter are four CACGTG motifs, which are potential binding sites for several transcription factors, including Myc, the Myc homologs Max, Mad and Mxi-1, USF, TFE3 and TFEB (see, for example, Zervos et al., supra, 1993; Gregor et al., *Genes Devel.* 1730–1740 (1990); Fisher et al., *Genes Devel.* 5:2342–2352 (1991)).

Characterization of the entire bax promoter (SEQ ID NO: 1) reveals binding sites for Myb (-2172 to -2167; -3845 to -3840; -3664 to -3659) AP-1 (-2165 to -2159; -2138 to -2132); Egr-1 (-44 to -36); NF-IL-6 (-2886 to -2878; -2087 to -2079; -1178 to -1170); NF-κB (-702 to -693; -687 to -679; -657 to -648; -76 to -68) In addition, characterization of the bax promoter reveals binding sites for Oct-1 (-3604 to -3597); Ets-1 (-3608 to -3601); PEA3 (-3591 to -3586; -2258 to -2253; -1662 to -1657; -582 to -577); MyoD (-2310 to -2305 and -1825 to -1820; Pit-1 (-1459 to -1452); half-sites for the estrogen receptor (-2533 to -2529; -2265 to -2261; -1922 to -1918; -1328 to -1324; -150 to -146); and binding sites for CACGTG binding proteins such as MyoD (-192 to -187; -147 to -142; -99 to -94; and -68 to -63) as indicated in FIG. 1.

B. Plasmid constructions

This section describes p53 expression plasmids and methods for making CAT reporter constructs containing various portions of the bax promoter.

The p53 expression plasmids, CMV-p53$_{wt}$ and CMV-p53$_{179}$, and the reporter plasmid, pFSVCAT, which contains six copies of the consensus p53 binding sequence and is regulated by p53 tumor suppressor, are described by Mietz et al., *EMBO J.* 11:5013–5020 (1992) and by Unger et al., *EMBO J.* 11:1383–1390 (1992), each of which is incorporated herein by reference. The plasmid pCMVβ-Gal, which expresses β-gal and is not regulated by p53, was used as a control for transfection (MacGregor and Caskey, *Nucl. Acids Res.* 17:2365 (1989), which is incorporated herein by reference).

Plasmid pUCSVOCAT contains a chloramphenicol acetyltransferase (CAT) reporter gene and a Hind III cloning site located upstream of the CAT gene (Fukamizu et al., *Biomed. Biochim. Acta* 50:659–663 (1991), which is incorporated herein by reference). A 371 bp SmaI-SacI fragment, representing positions -687 bp to -318 of the bax promoter (SEQ ID NO: 7), was obtained from pTM604-4 and subcloned by blunt-end ligation into the Hind III site of the promoterless CAT plasmid pUCSVOCAT (Fukamizu et al., supra, 1991) to produce pTM667-3. pTM604-4 contains a 4 kb Bam HI fragment that includes the upstream region of the bax gene as well as exon 1.

A 94 bp DdeI-DdeI fragment from pTM604-4, which contains positions -508 to -415 of the bax promoter (SEQ ID NO: 8), was subcloned by blunt-end ligation into the Bgl II site of the minimal promoter CAT reporter plasmid pA10-CATBS (Spalholz et al., *J. Virol.* 61:2128–2137 (1987), which is incorporated herein by reference) to produce the plasmid pTM672-6. pA10-CATBS contains an SV40 early-region promoter in which the enhancer is deleted.

Oligonucleotides having the sequences 5'-GATCTCACAAGTTAGAGACAAGCCTG-3' (SEQ ID NO: 9; oligomer A) and 5'-TCGACAGGCTTGTCTCTAACTTGTGA-3' (SEQ ID NO: 10; oligomer B), which correspond to positions -485 to -465 of bax, were annealed. The annealed DNA fragment, which has overhanging 5'-ends compatible with Bgl II and Sal I, was subcloned into the Bgl II and Sal I sites of pA10-CATBS to produce pTM672-14.

pTM672-18 was produced by annealing the oligonucleotides 5'-GATCGAGACCAAGCCTGGGCGTGGGCTATATTG-3' (SEQ ID NO: 11; oligomer C) and 5'-TCGACAATATAGCCCACGCCCAGGCTTGTCTC-3' (SEQ ID NO: 12; oligomer D), to produce a fragment corresponding to positions -474 to -449 of the bax promoter (SEQ ID NO: 13). The annealed fragment was subcloned into the Bgl II and Sal I sites of pA10-CATBS.

Oligomers A and D also were annealed, the overhanging 5'-ends were filled-in with Klenow fragment in the presence of all four deoxyribonucleotide triphosphates, the 5' ends were phosphorylated using T4 DNA kinase and ATP and the resulting fragment was subcloned by blunt-end ligation into the Bgl II site of pA10-CATBS to produce pTM686-4, which is a reporter construct containing positions -485 to -449 of the bax promoter (SEQ ID NO: 2).

A CAT construct containing mutations in the p53 binding site was made by introducing four nucleotide substitutions into the consensus p53 sequence. The 94 bp Dde I fragment was isolated and mutations were introduced by site-directed mutagenesis using a PCR overlap extension technique (Ho et al., *Gene* 77:51–59 (1989), which is incorporated herein by reference).

Oligonucleotide primers for site-directed mutagenesis were 5'- GAAGATCTGAGACGGGGTTATCTCTT-3' (SEQ ID NO: 14; Bgl II site underlined); 5'CGCGTCGACTGAGTGGTTTTGTTTTTT-3' (SEQ ID NO: 15; Sal I site underlined); 5'-AAGTTAGAGATAATGCTGGGCGTAGG-3' (SEQ ID NO: 16; and 5'-CCTACGCCCAGCATTATCTCTAACTT-3' (SEQ ID NO: 17). pTM604-4 was used as a template, and amplification was performed using Pfu heat-stable DNA polymerase (Stratagene, Inc.) as suggested by the manufacturer. The PCR product was gel-purified, digested with Bgl II and Sal I and subcloned into the Bgl II and Sal I sites of pA10-CATBS to produce pTM688-2. The presence of the mutations was confirmed by DNA sequencing.

C. The bax promoter and a portion of the bax promoter confer regulatory activity upon a linked gene This section describes methods for identifying portions of the bax promoter involved in p53-mediated gene regulation.

Cell lines were maintained between 10% and 90% confluence in medium containing 10% FBS, 1 mM L-glutamine, 100 u/ml penicillin-G and 50 µg/ml streptomycin at 37° C. in 5% $CO_2$ /95% air. HeLa and Saos-2 cells were grown in DMEM; H358 and TSU-prl were grown in RPMI-1640 (Mediatech; Washington D.C.). Saos-2 cell cultures also were supplemented with 1 mM Na-pyruvate and 1× non-essential amino acids (Hazelton Biologics, Inc., Lenexa, Kans.).

Cells were grown to approximately 70% confluence in 6 well (35 mm) plates. Transfection was performed by adding 30 µg "LIPOFECTIN"™ (GIBCO/BRL), 3 µg CAT reporter gene plasmid, 1 µg pCMVβ-Gal plasmid and 3 µg either pCMV-p53$_{wt}$, pCMV-p53$_{179}$ or pRc/CMV plasmid DNA for 16 hr, essentially as described by Miyashita et al. *Canc. Res.* 54:3131–3135 (1994b), which is incorporated herein by reference). After 48 hr, transfected cells were washed in HBSS, resuspended in 50 µl 0.25M Tris, pH 7.8, subjected to 3 freeze-thaw cycles and centrifuged at 16,000×g for 5 min to obtain supernatants for measurements of CAT and β-gal activity as described below (see, also, Miyashita et al., supra, 1994b).

CAT assays were performed by adding 30 µl of the cell lysate supernatant to a 70 µl reaction mixture containing 10 mM HCl, 43 mM acetyl-coenzyme A, 0.2 mCi (acetyl-$^3$H)-coenzyme A (4.48 Ci/mmol; NEN) and 0.7 mM chloramphenicol in a 96-well plate and incubating at 37° C. for 1 hour. The reaction was stopped by adding 100 µl of 7M urea, the reaction mixtures were transferred to scintillation vials containing 2 ml of toluene scintillator and radioactivity was measured using a scintillation counter as described by Phahl et al., *Meth. Enzymol.* 189:267–270 (1990), which is incorporated herein by reference.

β-gal assays were performed by adding 10 µl of the cell lysate supernatant to a 190 µl reaction mixture containing 0.35% of 2-mercaptoethanol and 0.7 mg/ml of o-nitrophenyl-β-D-galactopyranoside in a 96-well plate and incubating at 37° C. for 30–60 min. β-gal activity was measured using an ELISA plate reader at a wavelength of 405 nm as described by Phahl et al., supra, 1990.

For CAT assays and β-gal assays, serial dilutions of standard enzyme were included to verify that the results were within the linear phase of the reactions. In some experiments, the volume of the cell lysate supernatant added to the reaction was adjusted to obtain results within the linear range. Since p53 does not affect β-gal expression from pCMVβ-gal, CAT activity was normalized for β-gal activity. Normalization for protein concentration yielded comparable results.

In initial experiments, plasmid pTM667-3, which contained nucleotides -687 to -318 of the bax promoter (SEQ ID NO: 7), including the TATAA box, transcription start site and the consensus p53 binding sites, inserted upstream of the CAT gene, was cotransfected into various p53-deficient human tumor cell lines with an expression plasmid encoding either wild-type p53 (pCMV-p53$_{wt}$), the mutant inactive form of p53$^{179}$ (pCMV-p53$_{179}$) or no p53 protein (pRc/CMV).

Transient transfection assays also were performed using human lung cancer-derived H358 cells, which have a homozygous deletion of p53 genomic DNA sequences and do not produce any detectable p53 mRNA or protein (p53-null) (Takahashi et al., *Science* 248:491–494 (1989), which is incorporated herein by reference). In H358 human lung cancer cells, co-transfection of pTM667-3 with pCMV-p53$_{wt}$ resulted in strong trans-activation, with an approximately 60×increase in CAT activity compared to cells co-transfected with pCMV-p53$_{179}$ or pRc/CMV. Similar results were obtained with every other tumor line tested. For example, wild-type but not mutant p53$^{179}$ produced about a 30 fold increase in CAT activity in p53-deficient Saos-2 osteosarcoma cells containing pTM667-3. In addition, wild-type p53 expression resulted in trans-activation of pTM667-3 in HeLa cells, which have reduced p53 activity due, in part, to expression of the human papillomavirus E6 protein in these cells (Liang et al., *Oncogene* 8:2645–2652 (1993)), and in p53-deficient Tsu-prl prostate cancer cells. These results demonstrate that nucleotides -687 to -318 of the bax promoter (SEQ ID NO: 7) can confer activity on a linked gene. Wild-type p53 can up-regulate gene expression through this portion of the bax promoter in a variety of types of human tumor cell lines.

The activity of nucleotides -687 to -318 of the bax promoter (SEQ ID NO: 1) was further delineated by examining the expression of CAT from constructs containing various portions of the bax promoter as described in Example II.B. Expression of CAT constructs containing the 94 bp Dde I fragment (SEQ ID NO: 8; positions -508 to -415 of the entire bax promoter SEQ ID NO: 1) was up-regulated approximately 6 to 8 fold when cotransfected with pCMV-p53$_{wt}$ as compared to cells that received plasmids encoding the mutant p53$^{179}$ or no p53 protein. Expression of CAT constructs containing mutations in the potential p53-binding sites was unresponsive to p53. These results indicate that the -508 to -415 sequence (SEQ ID NO: 8) also confers p53-dependent up-regulation on a linked heterologous promoter.

The four potential p53 binding sites in the bax promoter are contained within a 37 bp region (SEQ ID NO: 2; positions -485 to -449 of SEQ ID NO: 1). Cotransfection of a CAT construct containing the entire 37 bp sequence into H358 cells with a plasmid encoding wild-type p53 produced an approximately 10×to 15×increase in CAT activity. In contrast, H358 cells cotransfected with this CAT construct and a plasmid expressing the mutant p53$^{179}$ protein or no p53 protein showed minimal CAT activity (FIG. 10). These results establish that the 37 bp sequence at positions -485 to -449 of the bax promoter (SEQ ID NO: 2) confers p53-mediated regulation upon a heterologous gene.

CAT constructs containing either the 5'- or 3'-half of the 37 bp portion of the bax promoter (SEQ ID NO: 2) also were cotransfected with the various p53 expression plasmids. The 5-half CAT construct contains positions -485 to -465 bp (SEQ ID NO: 18), which includes the perfect 10 bp consensus p53 binding sequence flanked upstream by one imperfect sequence (7/10 matches). The 3'-half CAT construct contains positions -474 to -449 (SEQ ID NO: 13), which includes the perfect 10 bp consensus sequence and two downstream imperfect potential p53 binding sites.

In comparison to the results obtained using the 37 bp portion of the bax promoter (SEQ ID NO: 2), which conferred about a 10 to 15 fold increased level of CAT gene expression, wild-type p53 induced about a 2 to 5 fold up-regulation of CAT activity from constructs containing either the 5'-half or 3'-half of the active fragment (SEQ ID NO: 2). These results demonstrate that a nucleotide sequence consisting of a perfect 10 bp consensus p53 sequence and at least one imperfect p53 sequence also can confer p53-mediated up-regulation on a heterologous gene. Cotransfection experiments performed with the minimal promoter plasmid, pA10-CAT, lacking any elements from the bax gene confirmed the specificity of these results.

D. The p53 protein binds a portion of the bax promoter containing a p53-RE

This section describes a method for determining that wild-type p53 specifically binds to a portion of the bax promoter.

In vitro-translated wild-type and mutant p53$^{179}$ proteins were prepared from RNA generated using the T7 RNA polymerase binding sites in the plasmids pCMV-p53$_{wt}$ and pCMV-p53$_{179}$. Coupled in vitro transcription/translation reactions were performed using T7 RNA polymerase and reticulocyte lysates (TNT-"LYSATE"™ ;

Promega, Inc., Madison, Wis.) as suggested by the manufacturer. Oligomers A and D were annealed and filled-in and radiolabelled using Klenow fragment in the presence of dATP, dGTP, TTP and α-$^{32}$P-dCTP.

A mutant DNA probe also containing four nucleotide substitutions was prepared using 5'-GATCTCACAATTTAGAGATAATGCTG-3' (SEQ ID NO: 19) and 5'-TCGACAATATAGCCTACGCCCAGCATTATCTC-3' (SEQ ID NO: 20) oligomers. The mutant DNA probe contains nucleotide substitutions in three of the four p53 binding site motifs.

Approximately 5 µl of the p53 protein-containing translation product was preincubated with no further additions or with the following monoclonal antibodies: either a combination of 0.5 µg anti-p53 IgG2$_a$ clone DO-1 (Santa Cruz Biotechnology, Inc., Santa Cruz, Calif. ) and 0.5 µg P421 (Oncogene Science, Inc., Uniondale, N.Y.) or 1 µg anti-CD2 control IgG$_{2a}$ antibody Leu-5b (Becton-Dickinson, Inc., San Jose, Calif. ). The reactions were incubated for 10 min at 25° C. with 0.5 µg sonicated salmon sperm DNA and 7 µl EMSA buffer (20 mM HEPES, pH 7.5, 0.1M NaCl, 1.5 mM MgCl$_2$, 10 mM dithiothreitol, 20% glycerol, 0.1% Triton X100, 1 mM PMSF, 10 ug/ml pepstatin, 10 ug/ml leupeptin). The $^{32}$P-labelled DNA probes (4×10$^5$ cpm) were added and incubation was continued for 20 min at 25° C. Following incubation, the samples were separated by electrophoresis in non-denaturing 4% polyacrylamide gels using 1×TBE, then the gels were dried and exposed to X-ray film (XAR; Kodak, Inc., New Haven, Conn.) at −80° C. with intensifying screens.

Binding assays were performed using the 37 bp portion of the bax promoter (SEQ ID NO: 2) or a sequence containing a mutant p53 binding element with wild-type or mutant p53$^{179}$ protein. Anti-p53 antibodies were included in some experiments to stabilize the in vitro interaction of p53 with the target DNA (Hupp et al., Cell 71:875–886 (1992), which is incorporated herein by reference). A moderate amount of non-specific binding of the in vitro-translated proteins occurred with both the wild-type and mutant DNA probes, regardless of whether p53 protein was present in the translation mixture.

When the binding reaction was performed using a combination of wild-type p53 protein, wild-type DNA probe and anti-p53 antibody was employed, a complex with shifted gel-mobility was detected. No complex was observed when either the anti-p53 antibody or p53 protein was eliminated from the reaction. Furthermore, no complex formation was observed when substitution of either 1) mutant p53 for wild-type p53 protein, 2) mutant DNA probe for the wild-type portion of the bax promoter (SEQ ID NO: 2), or 3) an isotype- and subclass-matched monoclonal antibody to CD2 for the anti-p53 antibody was made in the reaction. These results demonstrate that p53 specifically interacts with the 37 bp portion of the bax promoter (SEQ ID NO: 2) and indicate that the up-regulation conferred by the this sequence as demonstrated using the CAT assays described above is due to p53 binding.

EXAMPLE III

Screening Assays for Identifying an Agent that Effectively Increases Bax Gene Expression This example describes screening assays that are useful for identifying an agent that can act as a p53 analog and, therefore, can induce apoptosis in a cell.

A. Cotransfection assay using a p53-null cell line

Cotransfection of a p53-null cell line such as H358 cells with a plasmid expressing a mutant p53 protein such as a temperature-sensitive p53 protein (Yonish-Rouach et al., supra, 1991) and a plasmid containing a portion of a bax gene with a p53-RE operably linked to a reporter gene such as CAT is useful for obtaining a cell line that can be used to screen for an agent that effectively increases the level of cell death in a population of cells. The cell line obtained following transfection provides a well defined system having a known p53 protein and a defined portion of the bax promoter.

A screening assay using a cell line such as the one described above is particularly useful for identifying an effective agent that either 1) confers upon a mutant p53 protein the ability to act like a wild-type p53 tumor suppressor or 2) itself acts as a p53-analog in regulating bax gene expression. These different mechanisms of action can be distinguished using the assay described in Example III.C. An additional advantage of this cell line is that a sample of the cells can be incubated at the permissive temperature, which allows for expression of wild-type p53 tumor suppressor. Thus, the level of regulation achieved by wild-type p53 and can be compared to the level of regulation obtained by various potentially effective agents.

Typically, the assay is performed in 96-well plates, which allows screening of a large number of agents in parallel. Various reporter genes can be used in the assay. However, a gene such as the luciferase gene provides the advantage that, following addition of the agent, the 96-well plates can be automatically scanned by a luminescence detector to identify those agents that desirably modulate the level of expression of the reporter gene. For example, if a portion of the bax gene containing a p53-RE is linked to a reporter gene, an effective agent would increase the level of expression of the reporter gene.

In some cases, an agent that is determined to be an effective agent in this assay can be further examined using the following assay, which provides the advantage that the effective agent can be examined in a cell obtained from a patient.

B. Transfection assay using a cell line that expresses a mutant p53 protein

This assay uses a cell such as a tumor cell that expresses a mutant p53 gene and is obtained from a cancer patient. In this case, the cell is transfected only with a plasmid containing a portion of the bax promoter with a p53-RE linked to a reporter gene. Subsequently, various agents are screened as described above. This assay is particularly advantageous in that an effective agent obtained using the assay of Example II.A. can be screened for its ability to induce apoptosis in a particular tumor cell obtained from a patient.

Thus, the assay allows the selection of the most effective agent for a particular patient.

In addition, the assay can be used to select, from a pre-selected panel of effective agents, an effective agent that most effectively induces apoptosis in the particular patient's cancer cells. In this case, it is desirable to have previously screened agents using, for example, the cotransfection assay described above and to have preselected potentially effective agents.

C. Transfection assay using a p53-null cell line

Transfection of a p53-null cell line with a plasmid containing a portion of the bax promoter with a p53-RE linked to a reporter gene provides a cell line that is useful for screening to identify an agent that acts as a p53 analog in a cell. The assay is performed as described in Example III.A. and can be used to identify an effective agent that can independently provide the function of a wild-type p53 in regulating expression of a gene containing a p53-RE. This assay can be particularly useful when the p53-null cells are obtained from a cancer patient and the effective agent that is identified can be used to treat the patient.

EXAMPLE IV

Screening Assays for Identifying an Agent that Effectively Inhibits p53-Mediated Regulation of the p53-RE This example describes screening assays that are useful for identifying an agent that can prevent the p53-mediated regulation of a gene containing the p53-RE and, therefore, can reduce or inhibit apoptosis in a cell.

A. Gel shift assay

The gel shift assay described above provides a simple and efficient method of screening various agents to identify an agent that effectively inhibits the ability of p53 to regulate expression of a gene containing the p53-RE. The method can be automated and, therefore, allows for the rapid screening of a large number of potentially effective agents.

These binding reactions are performed essentially as described in Example II.D., except that the reactions are performed in 96-well plates and various agents are added to the well as appropriate. Following incubation, the samples can be transferred in parallel to precast gels for separation of the reaction products. Effective agents are selected by identifying those agents that inhibit the binding of p53 to a p53-RE. If desired, the selected effective agents can be further examined using the assays described below.

B. Cotransfection assay using a p53-null cell line

Cotransfection of a p53-null cell line such as H358 cells with a plasmid expressing a wild-type p53 tumor suppressor and a plasmid containing the p53-RE linked to a reporter gene such as CAT can provide cells that are useful for identifying agents that effectively inhibit the ability of p53 to regulate expression of a gene containing a p53-RE. These assays are performed as described in Example III.A.

C. Transfection of a cell expressing a wild-type p53 tumor suppressor

Transfection of a cell that expresses wild-type p53 with a plasmid containing the p53-RE linked to a reporter gene can be used to identify an agent that inhibits apoptosis in a cell. This assay is particularly useful when the cell that is transfected is particularly susceptible to cell death. An example of such a cell is a neuronal cell obtained, for example, from a patient with amyotrophic lateral sclerosis. In this case, an effective agent that is selected based on the particular cell type to be treated.

Although the invention has been described with reference to the disclosed examples, it should be understood that various modifications can be made without departing from the spirit of the invention. Accordingly, the invention is limited only by the following claims.

I claim:

1. An isolated bax promoter having the nucleotide sequence shown as position -3885 to position -1 in FIG. 1 (SEQ ID NO: 1).

2. An isolated nucleic acid molecule, comprising a nucleotide sequence encoding a gene product operably linked to the bax promoter of claim 1.

3. An isolated bax promoter having the nucleotide sequence shown as position -3885 to position -974 in FIG. 1 (SEQ ID NO: 1).

4. An isolated nucleic acid molecule, comprising a nucleotide sequence encoding a gene product operably linked to the bax promoter of claim 3.

5. An isolated active fragment of a bax promoter having at least 15 contiguous nucleotides of SEQ ID NO: 1, at least one nucleotide of the nucleotide sequence shown as position -3885 to position -974 in FIG. 1 (SEQ ID NO: 1).

6. An isolated nucleic acid molecule, comprising a nucleotide sequence encoding a gene product operably linked to the active fragment of claim 5.

7. The isolated active fragment of claim 5, said fragment having at least 20 contiguous nucleotides of SEQ ID NO: 1.

8. The isolated active fragment of claim 5, said fragment having at least 30 contiguous nucleotides of SEQ ID NO: 1.

9. A method of identifying an effective agent that regulates the level of expression in a cell of a gene operably linked to an entire bax promoter or an active fragment of a bax promoter having at least 15 contiguous nucleotides of SEQ ID NO: 1, said contiguous nucleotides including at least one nucleotide of the nucleotide sequence shown as position -3885 to position -974 in FIG. 1 (SEQ ID NO: 1), said method comprising the steps of:

(a) introducing into the cell a nucleic acid molecule comprising said gene operably linked to said bax promoter or said active fragment thereof, (b) determining a control level of expression of said gene in said cell containing said gene;

(c) contacting a corresponding cell containing said gene with an agent suspected of being an effective agent; and (d) determining a test level of expression of said gene in said cell of step (c) contacted with said agent, wherein a difference in said level of expression as compared to said control level of expression identifies said agent as an effective agent.

10. The method of claim 9, wherein said gene is a reporter gene.

11. The method of claim 9, wherein said bax promoter or active fragment thereof or active fragment thereof has a nucleotide sequence select from the group consisting of the nucleotide sequence shown as position -3885 to position -1 in FIG. 1 (SEQ ID NO: 1) and the nucleotide sequence shown as position -3885 to position -974 in FIG. 1 (SEQ ID NO: 1).

12. The method of claim 9, wherein said test level of expression is reduced or inhibited as compared to said control level of expression.

13. The method of claim 12, wherein said cell is a p53-deficient cell.

14. The method of claim 12, wherein said cell expresses a p53 tumor suppressor.

15. The method of claim 14, wherein said cell that expresses a p53 tumor suppressor is selected from the group consisting of a neuron and a lymphocyte.

16. The method of claim 9, wherein said test level of expression is increased as compared to said control level of expression.

17. The method of claim 16, wherein said cell is a p53-deficient cell.

18. The method of claim 12, wherein said p53-deficient cell is a p53-null cell, which does not contain any p53 protein.

19. The method of claim 17, wherein said p53-deficient cell expresses a mutant p53 tumor suppressor that does not regulate expression of said bax promoter or said active fragment thereof.

20. The method of claim 19, wherein said p53-deficient cell expressing said mutant p53 tumor suppressor is obtained by introducing into a p53-null cell a nucleic acid sequence comprising a gene encoding a mutant p53 tumor suppressor, which is expressed in said cell.

21. The method of claim 17, wherein said p53-deficient cell is a tumor cell.

22. The method of claim 21, wherein said p53-deficient tumor cell is derived from a cancer patient.

23. The method of claim 16, wherein said cell expresses a p53 tumor suppressor.

24. The method of claim 23, wherein said cell that expresses a p53 tumor suppressor is a tumor cell.

25. The method of claim 24, wherein said tumor cell that expresses a p53 tumor suppressor is derived from a cancer patient.

* * * * *

UNITED STATES PATENT AND TRADEMARK OFFICE
CERTIFICATE OF CORRECTION

Page 1 of 2

PATENT NO. : 5,744,310
DATED : April 28, 1998
INVENTOR(S) : John C. Reed

It is certified that error appears in the above-indentified patent and that said Letters Patent is hereby corrected as shown below:

Title Page, line 2, TITLE, please delete "INDENTIFYING" and replace therefor with --IDENTIFYING--.

Column 1, line 2, please delete "INDENTIFYING" and replace therefor with --IDENTIFYING--.

Column 4, line 58, please delete "53" and replace therefor with --p53--.

Column 8, line 53, please delete "FIG 1." and replace therefor with --FIG 1).--.

Column 17, line 31, please delete "pLTRp53cGval135," and replace therefor with --pLTRp53cGval135,--.

Column 17, line 41, please delete "1.5x107" and replace therefor with --$1.5 \times 10^7$--.

Column 18, line 56, please delete "5'-GGAATTCGCGGTGATGGACGGGTCCGG-" and replace therefor with --5'-GG<u>AATTC</u>GCGGTGATGGACGGGTCCGG---.

UNITED STATES PATENT AND TRADEMARK OFFICE
CERTIFICATE OF CORRECTION

PATENT NO. : 5,744,310
DATED : April 28, 1998
INVENTOR(S) : John C. Reed

It is certified that error appears in the above-indentified patent and that said Letters Patent is hereby corrected as shown below:

Column 18, line 58, please delete "5'-GGAATTCTCAGCCCATCTTCTTCCAGA-" and replace therefor with --5'-GG<u>AATTC</u>TCAGCCCATCTTCTTCCAGA---.

Column 19, line 2, please delete "(1081)," and replace therefor with --(1981),--.

Column 22, line 22, please delete "5'-GAAGATCTGAGACGGGGTTATCTCTT-3'" and replace therefor with --5'-GA<u>AGATCT</u>GAGACGGGGTTATCTCTT-3'--.

Column 22, line 24, please delete "5'CGCGTCGACTGAGTGGTTTTGTTTTTT-3'" and replace therefor with --5'-CGC<u>GTCGAC</u>TGAGTGGTTTTGTTTTTT-3'--.

Column 40, line 20, CLAIM 18, please delete "claim 12," and replace therefor with --claim 17,--.

Signed and Sealed this

Tenth Day of April, 2001

Attest:

NICHOLAS P. GODICI

Attesting Officer    Acting Director of the United States Patent and Trademark Office

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
( A ) LENGTH: 3885 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:1:

| | | | | | | |
|---|---|---|---|---|---|---|
| GGATCCCTTG | AGCCCAGGAG | GTCGAGGTGG | CAGTGAGCCA | CAGTTGTGTC | ATTGCACTCC | 60 |
| AGCCTGGACG | ACAGAGGGAG | ATCCTGTCTC | AAAATAAATA | AATAAAAATA | AAAATAAACA | 120 |
| GTTTGACTT | CACAACTAGC | TAAAAAGTGT | ATTCCCTCAC | TCAGTGACTG | TACTGTTCAG | 180 |
| AGGTGTATAC | CTGCATTAAA | AGCCCTTTCC | TTCCTTCTCT | GTAACTGGAG | TAGGGAAGGG | 240 |
| CTATCTCATT | GGACTGGAGT | AACACACACA | GATAAAGCCG | GATGCAAAGT | TAACAGGAAA | 300 |
| CACTATTTCT | CTCAAGGATA | CGCTTTGTTT | GTTTTTTTTT | TGAGATGAAG | TCTCGCTCTG | 360 |
| TCACCCGAGG | TGGAGTGCAA | TGGCACGATC | TCTGCTCACT | GCAGNCTCTG | CCTCCTGGGT | 420 |
| TCAAGTGATT | CTCTGGCCTC | AGCCTCCCAA | GTAGCTGGGA | TTACAGGAGC | GCACCAGTAC | 480 |
| GCCCAGCTAA | TTTTTGNATT | TTTAGTAGAG | ACAGGGTTTC | ACCATGTTGG | CCAGGCTGGT | 540 |
| CTCAAACTCC | TGACCTCAGG | TGATCTNCCT | GTCTTGGNCT | CCCAAAGTGG | TGGGATTTCA | 600 |
| GGTGTGAGCC | ACCACGCTGG | CCAAGGACAT | GGTTTCTTAC | AGAGACTTTG | TTCTCTAAAT | 660 |
| TCATAAATTG | TTGGAAATTC | TATCAGTAAA | AATGAAACAT | CCGAGTCTTG | CTGACAGGAT | 720 |
| CTAATCCACT | TGATACAGAG | TAGCAGCCTT | GATTCCAAA | GCAGGTGCAC | AGCTTCAGAT | 780 |
| AAAGGGTTTC | TGGATGCAAC | ATTTCACATG | TACCTTCTTG | TTTCCAGCGA | TTCAGGACAC | 840 |
| TGGTTTCACT | TCACAGTCCT | GATCCAATGT | TGACCTTGCT | TTGCTCTAAG | CTATCATTTG | 900 |
| GTTGTCACCT | AAGCTCTACC | CTCCCCCTTT | ATCTTGGCTT | TTTCTTTTCT | TTTTTCTTTT | 960 |
| TGAGACAGGC | TCTTCCTCTG | TCACCCAGTC | TGATTGCAGT | GATGCAATTG | ATCACAGCTC | 1020 |
| ACGGCAGCCG | GGACCTCCCA | AGCTCAAACA | ATCTTCCCAC | CTCAGCCTCC | CAAGTAGCTG | 1080 |
| GGACTACAGG | CACGCACCAC | CACATCCAGC | TAATTTTCTT | TTTTTTCTGC | TTCCTTTTCT | 1140 |

```
TTTTGTTTTT  TTTTNAGATA  GAGGCTTGCT  CTGTTGCCCA  GGCTGGGGTG  CAGTGGCACG   1200
ATCTTGGCTC  ACTGCAACCT  CTGCCTCTTG  GGTTCAAGCG  ATTCTCCTGC  CTCAGCCTCC   1260
CAAGCAGCTG  GGACTGCAGG  CACGCGCCAC  CACTCCCAGC  TAATTTTTTT  GTATTTTTAG   1320
TGGAGACGGG  GTTTCGCCAT  GTTGGCTAGG  CTGGTCACAA  ACTCCTGACC  TCAGATGATA   1380
CACCCACTTC  GGCCTCCAC   ACAGCTGGTA  TTACAGGTGT  GAGCTACCAC  GCCCGGCCCC   1440
CCCTCCTTTC  TTTTGTTTTT  TAGTTGACAC  AGGGTCTCAC  CATGGTACAG  CCCAGGCTGG   1500
TCCTGAACTC  CTGGCTTCAG  GTGATCCTCC  TGCCTTGGCC  TCCCAAAGTG  CTGGGACTAT   1560
AGGAATGAGC  CATCACACCT  GGCCCCTTTC  TTCAATTTTC  AAATCAAACT  GATCCTTCAA   1620
GGTCAAGAGG  AAATACCTCC  TCTGAGAAGT  CTTCTCTGAA  TGTCAGAGGC  AGACAATGTT   1680
TGATTTCTGC  ATGCTCCCCA  ACATTCAATC  ATACAGTTAT  TGAATAACAC  ATTTTGAGAG   1740
ATAACTATGA  ATCAAGTAAC  ATGCTGGTTT  CTGGGAGNAA  TTGAGGACAA  ATTAACCTTG   1800
TGGAAATTTT  GGGTGGATGA  AAAAAACCAA  CATTAAATTA  AACACTGCA   CACATTTACA   1860
GCTGTGAGAA  GCATTACACA  TCCTGGGTGC  TATGCGAGCT  TTTTTTTTT   TTTTTTTTT    1920
TTGGAGTTGG  AGTTTCCCTC  TTGTTACTGA  GGCTGGAGAG  CAAGGTCACG  ATCTCGGCTC   1980
ACTGCAACCT  CTGCCTCCAG  ATTCAAACGA  TTCCCTGCC   TCAGCTCCCG  AGTAGCTGGG   2040
ACTACAGGTG  CCTGCCACCA  CACCTGGCTA  ATTTAGAATT  TTTAGTAGGG  ATAGGGTTTC   2100
ACCGTGTTGG  CCAGGCTGGT  CTCAAACTCC  TGACCTCAGG  TGATCTACCC  ATCTCGGNCT   2160
CCCAAAGTGC  TGGGATTACA  GAAGTGAGCC  ACTGAGCCCA  ACCAGGAGCT  TTTTCGAGAA   2220
AGAAGGAAGT  CCAAGAGATC  TTCCTGACAC  CCTAGTCTGA  CTCTGCCCTT  TGSCTGCTCA   2280
AAATTTCCCC  ATGCTTCCCA  GCGGSCTTCT  GGACATAGAT  CAAGTCCCTT  CTCTGACAGG   2340
CCCAAACCCT  TTATCATCTG  ATCCTAGCTC  ATTTTTCTGA  GTTTCCTTA   GTTGCTATTA   2400
TTTTCTGTCT  AAAGTGACAT  GTCATAATAT  TCATAAAGCA  CACAAGTCTT  ATGTGTACAG   2460
CTCAATGAAT  TGTAAATATG  TGTATWCCCG  GCCGGGCACA  GTGGCTCACG  CCTGTAATCC   2520
CAGCACTTTG  GGAGGGCGAG  GCAGGTGGAT  CACTTGAGGT  CAGGAGCTTG  AGACCAGCCT   2580
GACCAACATA  GTGAAACCCC  ATCTTTACTA  AAAATACAAA  ATTAGCTGGG  CGTGGTGTCG   2640
CATGCCTGCA  ATTCCAGCTA  CTTGGGAGGC  TGAGGCAGGA  GAATTGCTTG  AACCCGGAGG   2700
CAGAGGTTGC  AGTAAGCCAA  GATCGTGCCA  TTGCACTCCA  TCCTGGGCAA  CAAGAGCAAA   2760
ACTCCGTCTC  AAAATAATAA  TAATAATAAT  AATAATAATA  ATAATAATAA  TAATAATAAT   2820
AATGTGTATA  CCCATGTAAA  CACCATTCAG  ATAAAAATAT  GGCATATTTG  GGGCACCCGG   2880
GGAGTGTCTC  TTGTGGCCCC  TCCCCTCCAT  ACCCTGCTGA  TCTATCAGCA  CAGATTAGTT   2940
TCTGCCACTT  TTTAAACTTC  ATATTCCTTT  TCTTTTTACA  CAAACACAAA  CATTCGAGTC   3000
ATGACTGGGT  GGGGTGGCTC  AAGCCTGTAA  TCTCAGCACT  TTGGGAGGCC  AAGGTGCGAG   3060
GATCGCTTGA  GTCTGGGAGT  TCAGAGACCA  GCCTGGGCAA  CATAGAGAGA  CCTCATCTCC   3120
ACATAAAAAG  TTTTAAAAAT  TAACCAGGGG  CGGTGTAGTC  CCAGCTACTC  AGGAGGCTGA   3180
GGTGGGAGGC  TTCAGCCCGG  GAATTCCAGA  CTGCAGTGAG  CCATGATTGG  GCCACTGCAC   3240
TCCAGCCTGG  GCAACACAGT  GAGACCCTGT  CTCAAAAAAA  AAAAAAAAAA  AAAAAAAAA    3300
AACAGGAAAA  AACAAACAAA  CAGAAAAGCA  GGCCTGGCGC  GGTAGCTCAT  GCCTGTAATC   3360
CCAGCGCTTT  GGAAGGCTGA  GACGGGGTTA  TCTCTTGGGC  TCACAAGTTA  GAGACAAGCC   3420
TGGGCGTGGG  CTATATTGCT  AGATCCAGGT  CTCTGCAAAA  AACAAAACCA  CTCAGTTTTT   3480
AGTCATCTAT  AACGTCCTGC  CTGGAAGCAT  GCTATTTTGG  GCCTCTGAGC  TTTTGCACTT   3540
```

| GCTAATTCCT | TCTGCGCTGG | GGAGAGCTCA | AACCCTGCCC | GAAACTTCTA | AAAATGGTGC | 3600 |
| CTGGATAAAT | GAAGGCATTA | GAGCTGCGAT | TGGACGGGCG | GCTGTTGGAC | GGCGCCACTG | 3660 |
| CTGGCACTTA | TCGGGAGATG | CTCATTGGAC | AGTCACGTGA | CGGGACCAAA | CCTCCCGAGG | 3720 |
| GAGCGAGGCA | GGTGCGGTCA | CGTGACCCGG | CGGCGCTGCG | GGCAGCGGC  | CATTTTGCGG | 3780 |
| GGCGGCCACG | TGAAGGACGC | ACGTTCAGCG | GGCTCTCAC  | GTGACCCGGG | CGCGCTGCGG | 3840 |
| CCGCCCGCGC | GGACCCGGCG | AGAGGCGGCG | GCGGGAGCGG | CGGTG      |            | 3885 |

( 2 ) INFORMATION FOR SEQ ID NO:2:

( i ) SEQUENCE CHARACTERISTICS:
        ( A ) LENGTH: 37 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

TCACAAGTTA GAGACAAGCC TGGGCGTGGG CTATATT    37

( 2 ) INFORMATION FOR SEQ ID NO:3:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

RRRCWWGYYY    10

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GGAATTCGCG GTGATGGACG GGTCCGG    27

( 2 ) INFORMATION FOR SEQ ID NO:5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GGAATTCTCA GCCCATCTTC TTCCAGA    27

( 2 ) INFORMATION FOR SEQ ID NO:6:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Cys Pro Glu Leu Thr Leu Glu Gln Pro Pro Gln Asp Ala Ser Thr Lys
1               5                   10                  15
Lys Leu Ser Glu
            20
```

( 2 ) INFORMATION FOR SEQ ID NO:7:

( i ) SEQUENCE CHARACTERISTICS:
        ( A ) LENGTH: 370 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:7:

```
GGGAATTCCA GACTGCAGTG AGCCATGATT GGGCCACTGC ACTCCAGCCT GGGCAACACA     60
GTGAGACCCT GTCTCAAAAA AAAAAAAAAA AAAAAAAAAA AAAACAGGAA AAAACAAACA    120
AACAGAAAAG CAGGCCTGGC GCGGTAGCTC ATGCCTGTAA TCCCAGCGCT TTGGAAGGCT    180
GAGACGGGGT TATCTCTTGG GCTCACAAGT TAGAGACAAG CCTGGGCGTG GGCTATATTG    240
CTAGATCCAG GTCTCTGCAA AAACAAAAC CACTCAGTTT TTAGTCATCT ATAACGTCCT     300
GCCTGGAAGC ATGCTATTTT GGGCCTCTGA GCTTTGCAC TTGCTAATTC CTTCTGCGCT     360
GGGGAGAGCT                                                          370
```

( 2 ) INFORMATION FOR SEQ ID NO:8:

( i ) SEQUENCE CHARACTERISTICS:
        ( A ) LENGTH: 94 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:8:

```
TGAGACGGGG TTATCTCTTG GGCTCACAAG TTAGAGACAA GCCTGGGCGT GGGCTATATT     60
GCTAGATCCA GGTCTCTGCA AAAACAAAA CCAC                                  94
```

( 2 ) INFORMATION FOR SEQ ID NO:9:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
GATCTCACAA GTTAGAGACA AGCCTG                                          26
```

( 2 ) INFORMATION FOR SEQ ID NO:10:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

TCGACAGGCT TGTCTCTAAC TTGTGA 26

( 2 ) INFORMATION FOR SEQ ID NO:11:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GATCGAGACC AAGCCTGGGC GTGGGCTATA TTG 33

( 2 ) INFORMATION FOR SEQ ID NO:12:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

TCGACAATAT AGCCCACGCC CAGGCTTGTC TC 32

( 2 ) INFORMATION FOR SEQ ID NO:13:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:13:

AGACAAGCCT GGGCGTGGGC TATATT 26

( 2 ) INFORMATION FOR SEQ ID NO:14:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

GAAGATCTGA GACGGGGTTA TCTCTT 26

( 2 ) INFORMATION FOR SEQ ID NO:15:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

CGCGTCGACT GAGTGGTTTT GTTTTTT 27

(2) INFORMATION FOR SEQ ID NO:16:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

AAGTTAGAGA TAATGCTGGG CGTAGG      26

(2) INFORMATION FOR SEQ ID NO:17:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CCTACGCCCA GCATTATCTC TAACTT      26

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:18:

TCACAAGTTA GAGACAAGCC T      21

(2) INFORMATION FOR SEQ ID NO:19:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

GATCTCACAA TTTAGAGATA ATGCTG      26

(2) INFORMATION FOR SEQ ID NO:20:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

TCGACAATAT AGCCTACGCC CAGCATTATC TC      32